(12) United States Patent
Katsuhara et al.

(10) Patent No.: US 11,536,619 B2
(45) Date of Patent: Dec. 27, 2022

(54) SENSOR, BAND, ELECTRONIC DEVICE, AND WRISTWATCH-TYPE ELECTRONIC DEVICE

(71) Applicant: SONY CORPORATION, Tokyo (JP)

(72) Inventors: Tomoko Katsuhara, Kanagawa (JP); Hiroto Kawaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 763 days.

(21) Appl. No.: 16/330,456

(22) PCT Filed: Sep. 8, 2017

(86) PCT No.: PCT/JP2017/032508
§ 371 (c)(1),
(2) Date: Mar. 5, 2019

(87) PCT Pub. No.: WO2018/051917
PCT Pub. Date: Mar. 22, 2018

(65) Prior Publication Data
US 2021/0208012 A1 Jul. 8, 2021

(30) Foreign Application Priority Data
Sep. 13, 2016 (JP) .............................. JP2016-179007

(51) Int. Cl.
*G01L 1/14* (2006.01)
*G01L 1/08* (2006.01)

(52) U.S. Cl.
CPC .............. *G01L 1/146* (2013.01); *G01L 1/086* (2013.01)

(58) Field of Classification Search
CPC ....... G01L 1/146; G01L 1/086; G06F 3/0414; G06F 3/0412
(Continued)

(56) References Cited

U.S. PATENT DOCUMENTS 5,010,774 A * 4/1991 Kikuo .................... G06F 3/016
901/46
5,750,904 A 5/1998 Doemens et al.
(Continued)

FOREIGN PATENT DOCUMENTS

| JP | S61-202089 | 9/1986 |
| JP | S60-084532 | 12/1986 |

(Continued)

OTHER PUBLICATIONS

International Search Report prepared by the Japan Patent Office dated Sep. 21, 2017, for International Application No. PCT/JP2017/032508.
(Continued)

*Primary Examiner* — Octavia Davis Hollington
(74) *Attorney, Agent, or Firm* — Sheridan Ross P.C.

(57) ABSTRACT

A sensor includes: an electrostatic-capacity-type sensor electrode layer having a plurality of sensing units; a reference electrode layer opposed to one main face of the sensor electrode layer; and a deformable layer disposed between the reference electrode layer and the sensor electrode layer, the deformable layer being to deform elastically due to application of pressure. The deformable layer is recessed between the sensing units or discontinuous between the sensing units. The reference electrode layer has a shaped portion between the sensing units.

19 Claims, 16 Drawing Sheets

(58) Field of Classification Search
USPC ........................................... 73/862.46
See application file for complete search history.

(56) References Cited

U.S. PATENT DOCUMENTS

| | | | |
|---|---|---|---|
| 10,928,259 B2* | 2/2021 | Morita | G06F 3/045 |
| 11,029,221 B2* | 6/2021 | Kobayashi | B32B 27/34 |
| 2011/0120228 A1 | 5/2011 | Main et al. | |
| 2013/0234734 A1* | 9/2013 | Iida | G06F 3/0447 |
| | | | 324/661 |
| 2014/0150571 A1* | 6/2014 | Kuniyoshi | G01L 1/20 |
| | | | 156/280 |
| 2015/0070306 A1* | 3/2015 | Shinkai | G06F 1/1626 |
| | | | 345/174 |
| 2016/0239135 A1* | 8/2016 | Kawaguchi | G08C 17/00 |

FOREIGN PATENT DOCUMENTS

| | | |
|---|---|---|
| JP | H05-288619 | 11/1993 |
| JP | H10-504387 | 4/1998 |
| JP | 2007-315876 | 12/2007 |
| JP | 2014-142193 | 8/2014 |

OTHER PUBLICATIONS

Official Action (no English translation available) for Japanese Patent Application No. 2018-539684, dated Dec. 8, 2020, 5 pages.

* cited by examiner

SENSOR, BAND, ELECTRONIC DEVICE, AND WRISTWATCH-TYPE ELECTRONIC DEVICE

CROSS REFERENCE TO RELATED APPLICATIONS

This application is a national stage application under 35 U.S.C. 371 and claims the benefit of PCT Application No. PCT/JP2017/032508 having an international filing date of 8 Sep. 2017, which designated the United States, which PCT application claimed the benefit of Japanese Patent Application No. 2016-179007 filed 13 Sep. 2016, the entire disclosures of each of which are incorporated herein by reference.

TECHNICAL FIELD

The present technology relates to an electrostatic-capacity-type sensor, a band, an electronic device, and a wristwatch-type electronic device.

BACKGROUND ART

In recent years, electrostatic-capacity-type pressure sensors have been expected to be applied to various electronic devices. An electrostatic-capacity-type pressure sensor is generally formed by laminating a plurality of layers including films or the like (see, for example, Patent Document 1).

CITATION LIST

Patent Document

Patent Document 1: Japanese Patent Application Laid-Open No. 2007-315876

SUMMARY OF THE INVENTION

Problems to be Solved by the Invention

For a pressure sensor including a plurality of layers laminated as described above, when the pressure sensor is bent, a layer on the inner diameter side is subjected to compressive stress, whereas a layer on the outer diameter side is subjected to tensile stress, so that shear stress acts between the layers. Therefore, in a case where the pressure sensor is worn on a subject body such as a human body or an object, there is a possibility that separation occurs between the layers.

An object of the present technology is to provide a sensor capable of suppressing separation between layers, a band, an electronic device, and a wristwatch-type electronic device that include the sensor.

Solutions to Problems

In order to solve the above-mentioned problem, a sensor according to a first technology includes: an electrostatic-capacity-type sensor electrode layer having a plurality of sensing units; a reference electrode layer opposed to one main face of the sensor electrode layer; and a deformable layer disposed between the reference electrode layer and the sensor electrode layer, the deformable layer being to deform elastically due to application of pressure, in which the deformable layer is recessed between the sensing units or discontinuous between the sensing units, and the reference electrode layer has a shaped portion between the sensing units.

A sensor according to a second technology includes: an electrostatic-capacity-type sensor electrode layer having a plurality of sensing units; a first reference electrode layer opposed to a first main face of the sensor electrode layer; a second reference electrode layer opposed to a second main face of the sensor electrode layer; a first deformable layer disposed between the first reference electrode layer and the sensor electrode layer, the first deformable layer being to deform elastically due to application of pressure; and a second deformable layer disposed between the second reference electrode layer and the sensor electrode layer, the second deformable layer being to deform elastically due to application of pressure, in which the first deformable layer and the second deformable layer are recessed between the sensing units or discontinuous between the sensing units, and the first reference electrode layer and the second reference electrode layer each have a shaped portion between the sensing units.

A sensor according to a third technology includes: an electrostatic-capacity-type sensor electrode layer having a plurality of sensing units; a reference electrode layer opposed to one main face of the sensor electrode layer; and a plurality of elastic members, in which the elastic members each are provided between the reference electrode layer and the sensing unit, and the reference electrode layer has a shaped portion between the sensing units.

A band according to a fourth technology includes the sensor according to the first, second, or third technology.

An electronic device according to a fifth technology includes the sensor according to the first, second, or third technology.

A wristwatch-type electronic device according to a sixth technology includes a band having the sensor according to the first, second, or third technology.

Effects of the Invention

According to the present technology, separation between layers can be suppressed. Note that the effects described herein are not necessarily limited, and any of the effects described in the present disclosure may be applied.

MODE FOR CARRYING OUT THE INVENTION

Embodiments of the present technology will be described in the following order.
1 First Embodiment (example of a sensor)
2 Second Embodiment (example of a sensor)
3 Third Embodiment (example of a sensor)
4 Fourth Embodiment (example of a sensor)
5 Fifth Embodiment (example of an electronic device)

1 First Embodiment

[Configuration of Sensor]

Figure 1A:
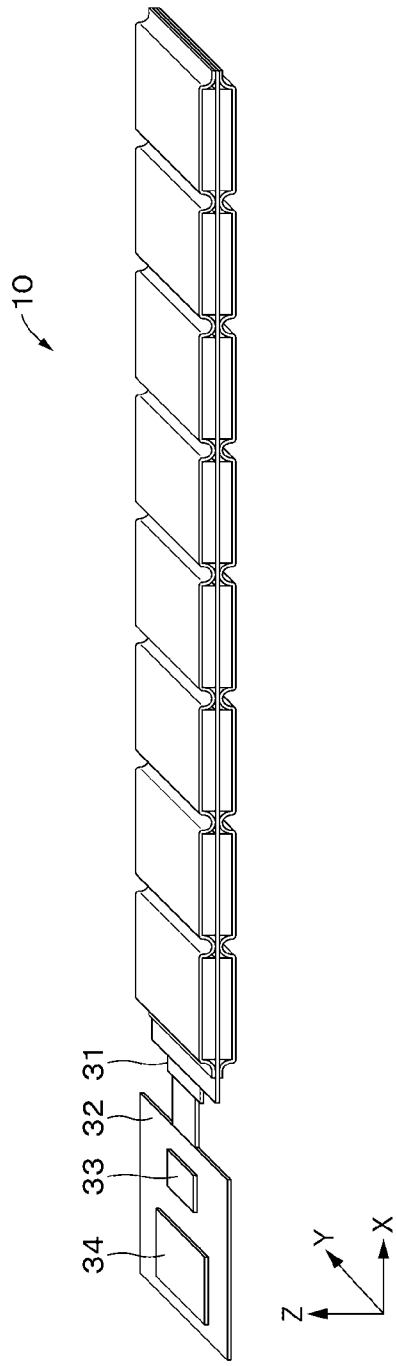
FIG. 1A is a perspective view illustrating the external appearance of a pressure sensor.

A sensor 10 according to a first embodiment of the present technology is a so-called pressure distribution sensor. As illustrated in FIG. 1A, the sensor 10 has an elongated sheet shape, and is capable of detecting pressure applied to both main faces of the sensor 10. The sensor 10 is electrically connected to a printed circuit board assembly (PCBA) 32 via a flexible printed circuit (FPC) 31. A controller integrated circuit (IC) 33 serving as a control unit and a central processing unit (CPU) 34 serving as a data processing unit are mounted on the PCBA 32. The PCBA 32 is mounted on the main body of an electronic device connected via the FPC 31.

Figure 1B:
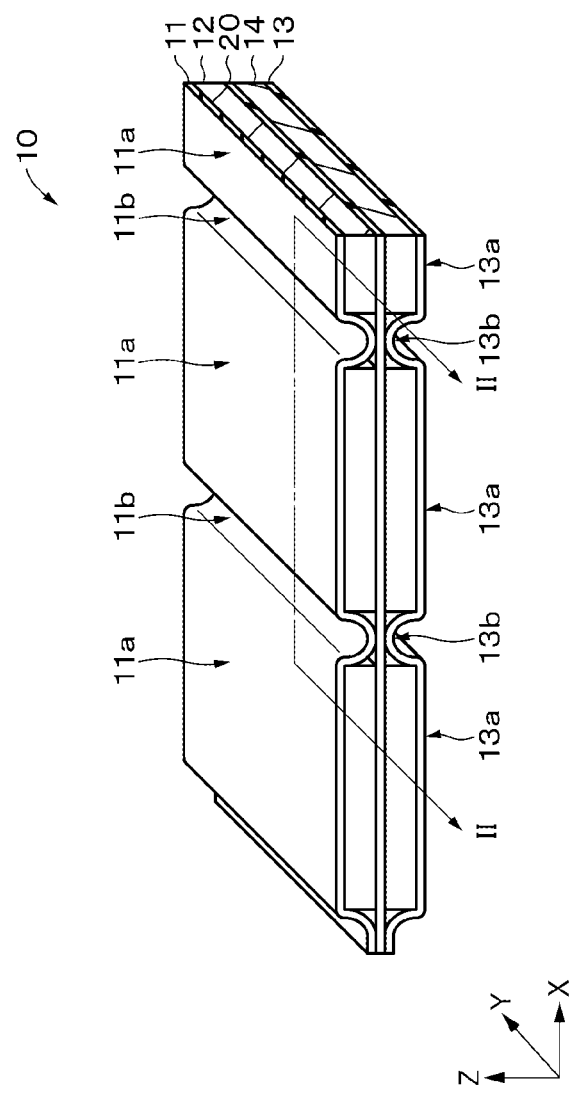
FIG. 1B is an enlarged perspective view of part of FIG. 1A.
Figure 2:
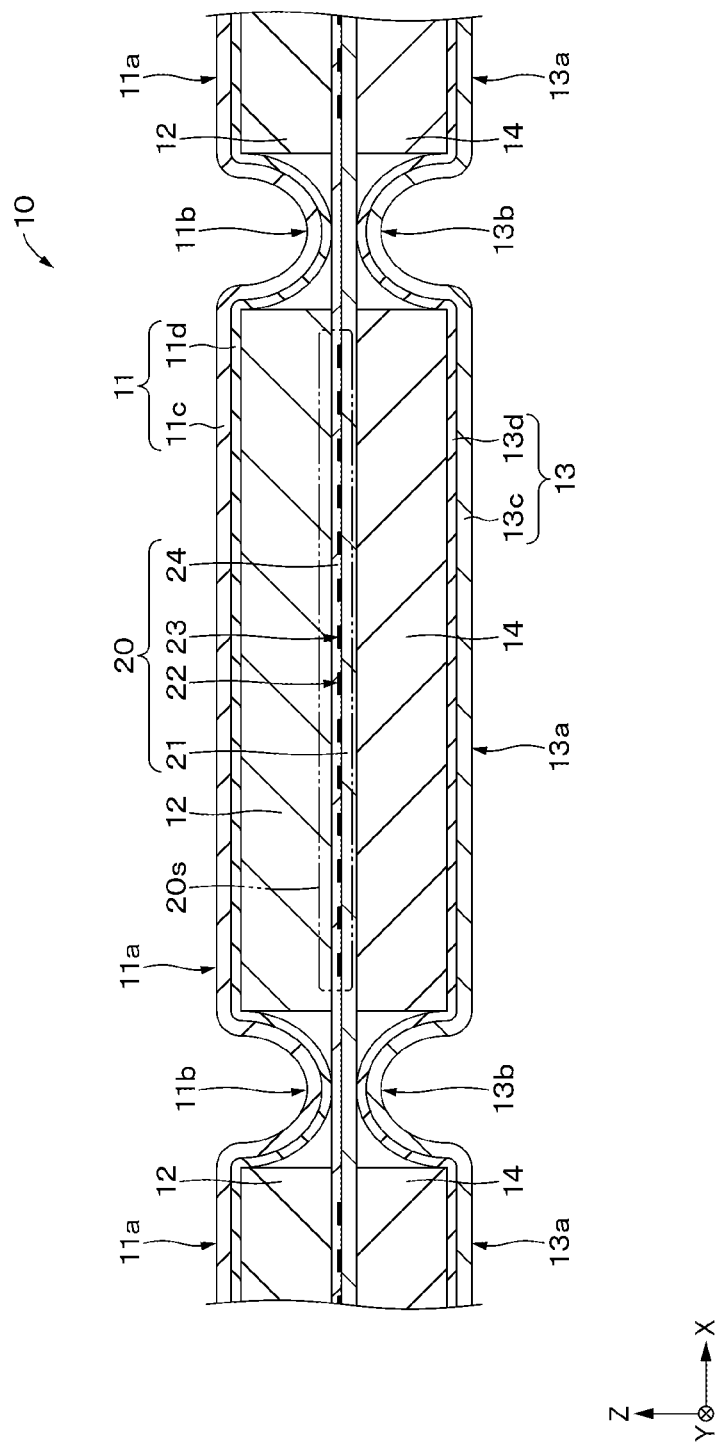
FIG. 2 is a cross-sectional view taken along line II-II in FIG. 1B.

As illustrated in FIGS. 1B and 2, the sensor 10 includes an electrostatic-capacity-type sensor electrode layer 20, electrode bases 11 and 13, and deformable layers 12 and 14. Note that, in the present specification, the longitudinal direction of the sensor 10 in a flat state is referred to as the ±X-axis direction, the width direction (lateral direction) is referred to as the ±Y-axis direction, and a direction perpendicular to the longitudinal direction and the width direction is referred to as the ±Z-axis direction.

The electrode base 11 and the sensor electrode layer 20 are disposed such that one main face of the sensor electrode layer 20 is opposed to one main face of the electrode base 11. The deformable layer 12 is provided between the one main face of the electrode base 11 and the one main face of the sensor electrode layer 20, and deforms elastically due to pressure applied to a main face of the sensor 10. The electrode base 13 and the sensor electrode layer 20 are disposed such that another main face of the sensor electrode layer 20 is opposed to one main face of the electrode base 13. The deformable layer 14 is provided between the one main face of the electrode base 13 and the other main face of the sensor electrode layer 20, and deforms elastically due to pressure applied to the main face of the sensor 10. The deformable layer 12 is stuck to the one main face of the sensor electrode layer 20 and the one main face of the electrode base 11 via an adhesive layer (not illustrated). Similarly, the deformable layer 14 is stuck to the other main face of the sensor electrode layer 20 and the one main face of the electrode base 13 via an adhesive layer (not illustrated).

The sensor 10 is suitable for use as a wearable sensor. For example, measurement of the pressure distribution inside the sensor 10 with the sensor 10 wound around an arm, a neck, a chest, an abdomen, a leg, or the like enables detection of a movement of the human body. Furthermore, aspiration, heartbeat, pulse, and the like can also be measured by detecting the vibration.

The sensor 10 is also suitable for use as a grip sensor. The sensor 10 is wound around a grip, whereby pressure applied when the grip is grasped by hand can be measured. The sensor 10 can be wound around grips of various thicknesses. For example, winding around a grip of a sport product such as a golf club or a tennis racket enables check of a state of a player, and winding around a handle, a control bar, or the like of a vehicle (for example, a bicycle, an automobile, a motorcycle, or the like), an aircraft, and a spacecraft, and the like enables check of a state of an operator. Furthermore, the sensor 10 is worn on a three-dimensional surface, whereby a sensing function can be imparted to the three-dimensional surface.

The controller IC 33 detects pressure applied to the main face of the sensor 10 on the basis of an output signal corresponding to electrostatic capacity supplied from the sensor 10, and outputs the detection result to the CPU 34. The CPU 34 is a main CPU or the like of the main body of the electronic device, and executes various types of processing on the basis of the detection result supplied from the controller IC 33.

Hereinafter, the sensor electrode layer 20, the electrode bases 11 and 13, and the deformable layers 12 and 14 included in the sensor 10 will be sequentially described.

(Sensor Electrode Layer)

Figure 3A:
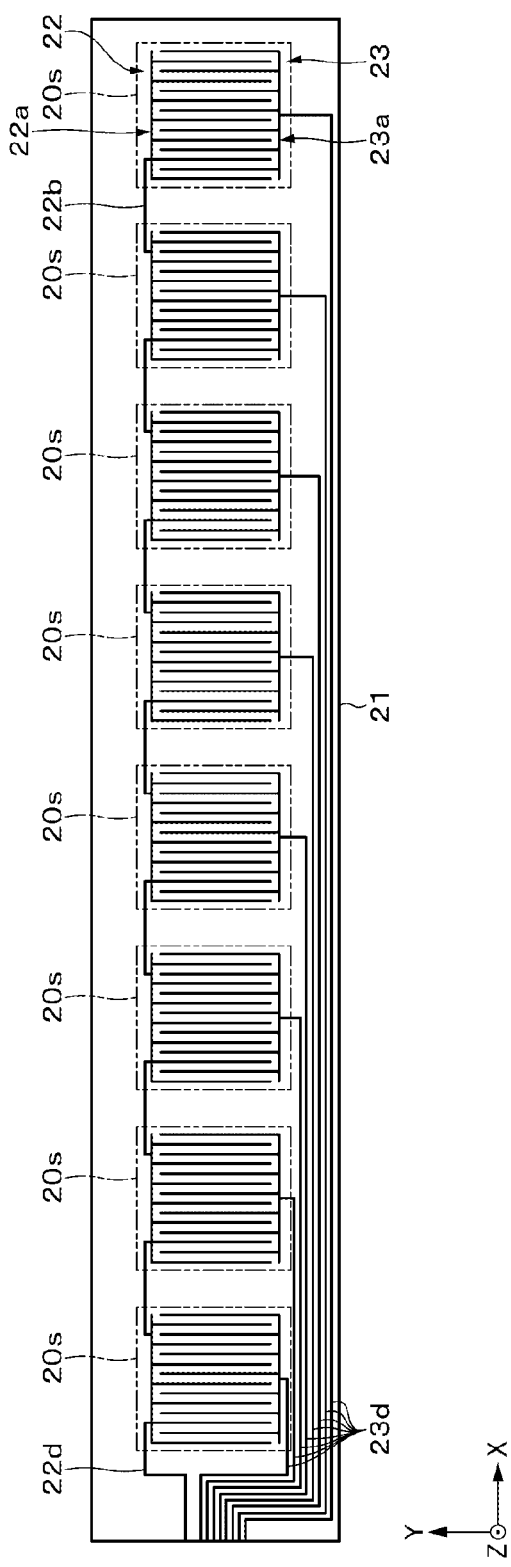
FIG. 3A is a plan view illustrating the configuration of a sensor electrode layer.

As illustrated in FIGS. 2 and 3A, the sensor electrode layer 20 includes a flexible base 21, one pulse electrode 22 and a plurality of sense electrodes 23 provided on one main face of the base 21, and an insulating layer 24 covering the pulse electrode 22 and the sense electrodes 23. A sensing unit 20s includes the pulse electrode 22 and the sense electrode 23. With a plurality of sensing units 20s in plan view in the Z-axis direction, the plurality of sensing units 20s is one-dimensionally disposed forming one array at equal intervals in the X-axis direction. Note that the sensor electrode layer 20 may not include the insulating layer 24, and the adhesive layer (not illustrated) provided between the deformable layer 12 and the sensor electrode layer 20 may also function as the insulating layer 24.

The base 21 has a film shape. In the present specification, the film also includes a sheet. As a material of the base 21, a polymer resin is preferably used. Examples of the polymer resin include: polyethylene terephthalate (PET); polyethylene naphthalate (PEN); polycarbonate (PC); acrylic resin (PMMA); polyimide (PI); triacetylcellulose (TAC); polyester; polyamide (PA); aramid; polyethylene (PE); polyacrylate; polyether sulfone; polysulfone; polypropylene (PP); diacetyl cellulose; polyvinyl chloride; epoxy resin; urea-formaldehyde resin; urethane resin; melamine resin; cyclic olefin polymer (COP); thermoplastic norbornene-based resin; and the like.

Figure 3B:
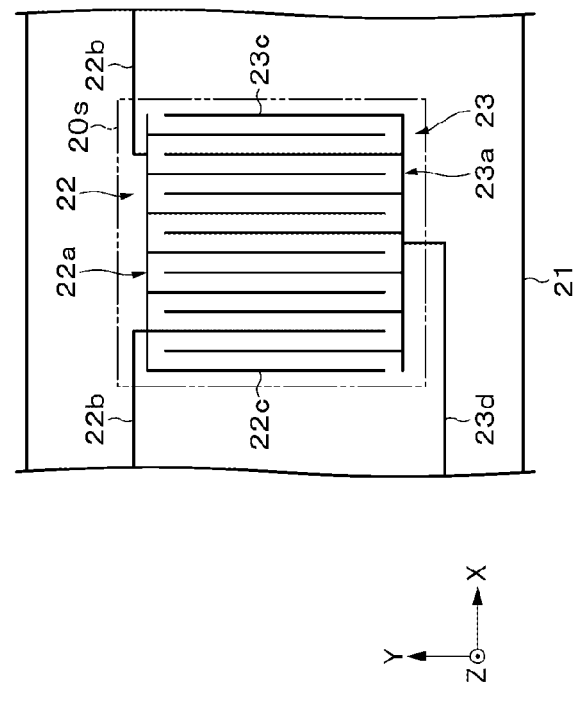
FIG. 3B is an enlarged plan view of part of FIG. 3A.

As illustrated in FIGS. 3A and 3B, the pulse electrode 22 as a first electrode includes a plurality of unit electrode bodies 22a and a plurality of connection portions 22b. The plurality of unit electrode bodies 22a is one-dimensionally disposed forming one array at constant intervals in the X-axis direction, and the unit electrode bodies 22a adjacent to each other are connected by the connection portions 22b. As illustrated in FIGS. 3A and 3B, each sense electrode 23 as a second electrode includes one unit electrode body 23a. The respective unit electrode bodies 23a included in the plurality of sense electrodes 23 are one-dimensionally disposed forming one array at constant intervals in the X-axis direction.

A wiring 22d is drawn out from one end of the pulse electrode 22 and connected to the FPC 31. A wiring 23d is also drawn out from one end of each sense electrode 23, routed around the peripheral portion of the one main face of the base 21, and connected to the FPC 31.

The unit electrode bodies 22a each have a comb-teeth shape in which a plurality of sub-electrodes 22c extends in the Y-axis direction. The unit electrode bodies 23a each have a comb-teeth shape in which a plurality of sub-electrodes 23c extends in the Y-axis direction. The unit electrode bodies 22a and 23a are disposed such that the sub-electrodes 22c interdigitate with the sub-electrodes 23c. Specifically, the plurality of sub-electrodes 22c and the plurality of sub-electrodes 23c are alternately disposed, and the adjacent sub-electrodes 22c and 23c are spaced apart from each other at predetermined intervals. The intervals between the sub-electrodes 22c and 23c may be constant or may vary. Each sensing unit 20s includes the unit electrode bodies 22a and 23a disposed interdigitating.

The insulating layer 24 contains at least one of an inorganic material or an organic material. Examples of the inorganic material that can be used include: $SiO_2$, SiNx, SiON, $Al_2O_3$, $Ta_2O_5$, $Y_2O_3$, $HfO_2$, HfAlO, $ZrO_2$, $TiO_2$, or the like. Examples of the organic material that can be used include: a polymer resin such as polyacrylate such as polymethyl methacrylate (PMMA), polyvinyl alcohol (PVA), polystyrene (PS), polyimide, polyester, epoxy, polyvinyl phenol, or polyvinyl alcohol.

(Electrode Base)

The electrode bases 11 and 13 are flexible electrode films. The electrode base 11 forms one main face of the sensor 10, and the electrode base 13 forms another main face of the sensor 10. The electrode bases 11 and 13 are uneven layers each having a protruding shape at a position opposed to the sensing unit 20s, the uneven layers each having a recessed shape at an opposed position between the sensing unit 20s and a sensing unit 20s.

The electrode base 11 includes an opposed portion 11a opposed to the sensing unit 20s and a shaped portion 11b provided between the opposed portion 11a and an opposed portion 11a. The deformable layer 12 is provided between the opposed portion 11a and the sensor electrode layer 20, the opposed portion 11a being held at a predetermined distance from the one main face of the sensor electrode layer 20 by the deformable layer 12. The shaped portion 11b is opposed to a portion between the adjacent sensing units 20s of the one main face of the sensor electrode layer 20. The shaped portion 11b is bent in a recessed shape being close to the one main face of the sensor electrode layer 20 with the sensor 10 held flat. As the shape of the shaped portion 11b bent in a recessed shape as described above, the shaped portion 11b is preferably curved in an arch shape toward the one main face of the sensor electrode layer 20. Here, the "bent" state includes a "folded" state.

The electrode base 13 includes an opposed portion 13a opposed to the sensing unit 20s and a shaped portion 13b provided between the opposed portion 13a and an opposed portion 13a. The deformable layer 14 is provided between the opposed portion 13a and the sensor electrode layer 20, and the opposed portion 13a is held at a predetermined distance from another main face of the sensor electrode layer 20 by the deformable layer 14. The shaped portion 13b is opposed to a portion between the adjacent sensing units 20s of the other main face of the sensor electrode layer 20. The shaped portion 13b is bent in a recessed shape being close to the other main face of the sensor electrode layer 20 with the sensor 10 held flat. As the shape of the shaped portion 13b bent in a recessed shape as described above, the shaped portion 13b is preferably curved in an arch shape toward the other main face of the sensor electrode layer 20.

Note that, instead of the shaped portion 11b that deforms in the recessed shape being close to the one main face of the sensor electrode layer 20, the electrode base 11 may include a shaped portion that deforms in a protruding shape being far from the one main face of the sensor electrode layer 20, or may include an uneven shaped portion obtained by combination of the recessed shape with the protruding shape described above. Furthermore, instead of the shaped portion 13b that deforms in the recessed shape being close to the other main face of the sensor electrode layer 20, the electrode base 13 may include a shaped portion deforms in a protruding shape being far from the other main face of the sensor electrode layer 20, or may include an uneven shaped portion obtained by combination of the recessed shape with the protruding shape described above. However, in consideration of covering the sensor 10 with a film-shaped exterior member or the like, the electrode bases 11 and 13 preferably include the recessed shaped portions 11b and 13b described above, respectively.

Examples of the shape in the X-Z cross section of the shaped portions 11b and 13b include, but are not limited to, a curved shape such as a U-shape or a substantially partial circular shape, a bent shape such as a V-shape or a W-shape, and the like. The shaped portions 11b and 13b may be slack or wrinkled, for example.

The shaped portion 11b may be formed by hot press molding or the like, may be formed by slackening the electrode base 11 between the deformable layer 12 and a deformable layer 12 adjacent thereto, or may be formed by imparting a wrinkle to the electrode base 11 between the adjacent deformable layers 12. Similar to the shaped portion 11b, the shaped portion 13b may also be formed by hot pressing, slackening, or wrinkling.

The electrode base 11 includes a flexible base 11c and a reference electrode layer (hereinafter referred to as "REF electrode layer") 11d provided on one main face of the base 11c. The electrode base 11 is disposed on the one main face side of the sensor electrode layer 20 such that the REF electrode layer 11d is opposed to the one main face of the sensor electrode layer 20. The electrode base 13 includes a flexible base 13c and a REF electrode layer 13d provided on one main face of the base 13c. The electrode base 13 is disposed on the other main face side of the sensor electrode layer 20 such that the REF electrode layer 13d is opposed to the other main face of the sensor electrode layer 20. The electrode bases 11 and 13 can be formed by, for example, hot press molding or the like.

The bases 11c and 13c each have a configuration similar to that of the base 21 described above. The REF electrode layers 11d and 13d are so-called ground electrodes and each have a ground potential. Examples of the shape of the REF electrode layers 11d and 13d include, but are not limited to, a thin film shape, a foil shape, a mesh shape, and the like. The bases 11c and 13c may each include a fabric.

Each of the REF electrode layers 11d and 13d may be a layer having electric conductivity, and for example, an inorganic conductive layer containing an inorganic conductive material, an organic conductive layer containing an organic conductive material, and an inorganic-organic conductive layer containing both of the inorganic conductive material and the organic conductive material, or the like can be used. The inorganic conductive material and the organic conductive material may be particles.

Examples of the inorganic conductive material include a metal, a metal oxide, and the like. Here, the metal is defined as including a semimetal. Examples of the metal include, but are not limited to, a metal such as aluminum; copper; silver; gold; platinum; palladium; nickel; tin; cobalt; rhodium; iridium; iron; ruthenium; osmium; manganese; molybdenum; tungsten; niobium; tantalum; titanium; bismuth; antimony; lead, and an alloy thereof; or the like. Examples of the metal oxide include, but are not limited to, indium tin oxide (ITO); zinc oxide; indium oxide; antimony-added tin oxide; fluorine-added tin oxide; aluminum-added zinc oxide; gallium-added zinc oxide; silicon-doped zinc oxide; zinc oxide-tin oxide based; indium oxide-tin oxide based; zinc oxide-indium oxide-magnesium oxide based; or the like.

Examples of the organic conductive material include a carbon material, a conductive polymer, or the like. Examples of the carbon material include, but are not limited to, carbon black; carbon fiber; fullerene; graphene; carbon nanotube; carbon microcoil; nanohorn; or the like. Examples of the conductive polymer that can be used include, but are not limited to, a substituted or unsubstituted polyaniline; polypyrrole; polythiophene; a (co) polymer containing one or two selected from these; or the like.

The REF electrode layers 11d and 13d may be thin films prepared through either a dry process or a wet process. Examples of the dry process that can be used include, but are not particularly limited to, a sputtering method, an evaporation method, or the like. Each of the electrode bases 11 and 13 may be a metal-deposited fabric, a plastic film laminated with aluminum foil, or the like.

The electrode base 11 is provided on the one main face side of the sensor electrode layer 20 and the electrode base 13 is provided on the other main face side of the sensor electrode layer 20, respectively. Thus, an external noise (external electric field) can be prevented from entering the sensor electrode layer 20 from both main face sides of the sensor 10.

(Deformable Layer)

The deformable layers 12 and 14 each have a film shape, and are intermittently provided being discontinuous between the adjacent sensing units 20s in the X-axis direction. Specifically, the deformable layers 12 and 14 are one-dimensionally disposed forming one array at constant intervals in the X-axis direction such that the deformable layers 12 and 14 overlap with the sensing unit 20s in the thickness direction (Z-axis direction) of the sensor 10, and a space is provided between the adjacent deformable layers 12. The deformable layer 12 is interposed between the one main face of the sensor electrode layer 20 and the opposed portion 11a, and the shaped portion 11b is disposed in the space between the deformable layers 12. The deformable layer 14 is interposed between the other main face of the sensor electrode layer 20 and the opposed portion 13a, and the shaped portion 13b is disposed in a space between the deformable layer 14 and a deformable layer 14.

For the sensor 10, the deformable layer 12 that is soft and elastically deformable is interposed between the one main face of the sensor electrode layer 20 and the one main face of the electrode base 11, and the deformable layer 14 that is soft and elastically deformable is interposed between the other main face of the sensor electrode layer 20 and the one main face of the electrode base 13, whereby the sensitivity and the dynamic range of the sensor 10 are adjusted.

The deformable layers 12 and 14 are films that deform elastically due to pressure applied to the main face of the sensor 10. The deformable layers 12 and 14 each include a dielectric such as a foamed resin or an insulating elastomer. The foamed resin is a so-called sponge, which is, for example, at least one of foamed polyurethane, foamed polyethylene, foamed polyolefin, sponge rubber, or the like. The insulating elastomer is, for example, at least one of a silicone-based elastomer, an acrylic-based elastomer, a urethane-based elastomer, a styrene-based elastomer, or the like.

With the deformable layers 12 and 14 in plan view in a direction perpendicular to the main faces (Z-axis direction), the deformable layers 12 and 14 each have a rectangular shape. However, the shape of the deformable layers 12 and 14 are not limited to this shape, and may be a circular shape, an elliptic shape, a polygonal shape other than the rectangular shape, an indefinite shape, or the like.

Note that, instead of at least one of the deformable layer 12 or the deformable layer 14, the sensor 10 may be provided with an elastic member that deforms elastically due to pressure applied to the main face of the sensor 10. The elastic member is a spring-shaped member such as a columnar body (pillar), a flat spring, or the like.

[State of Curved Sensor]

Next, a state where the sensor 10 according to the first embodiment of the present technology is curved will be described.

Figure 4A:
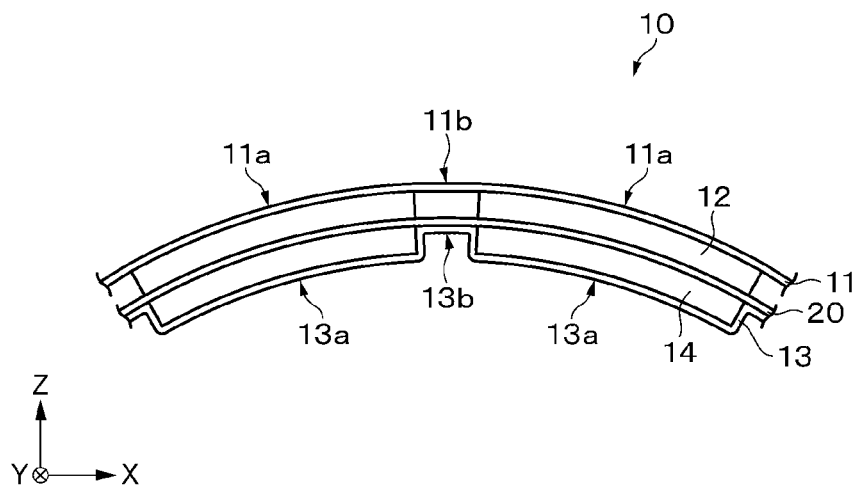
FIG. 4A is a side view illustrating the sensor curved such that one main face has a protruding shape.

As illustrated in FIG. 4A, when the sensor 10 is curved such that the one main face on the side where the electrode base 11 is provided has a protruding shape, the electrode base 11 deforms such that the recessed bend of the shaped portion lib is gentle or the shaped portion 11b is substantially flat. On the other hand, the electrode base 13 deforms such that the recessed bend of the shaped portion 13b is further increased or the shaped portion 13b is pressed against the other main face of the sensor electrode layer 20. With this arrangement, shear stress acting between the electrode base 11 and the deformable layer 12 and between the electrode base 13 and the deformable layer 14 can be reduced.

Figure 4B:
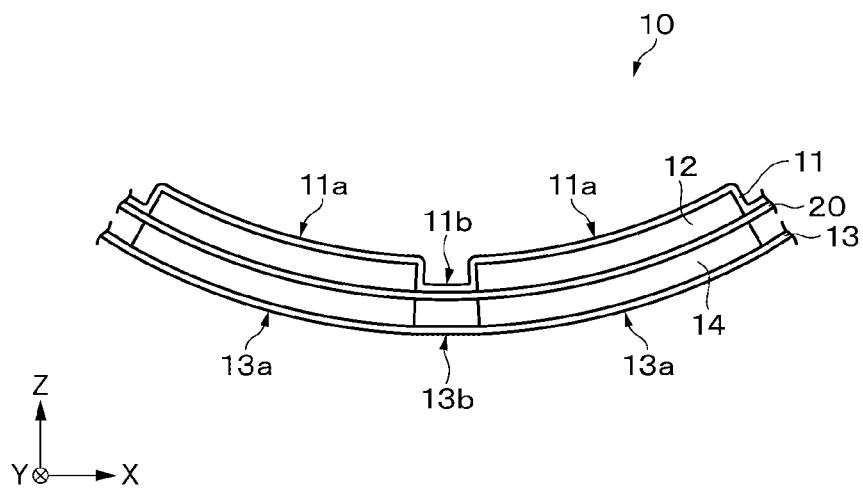
FIG. 4B is a side view illustrating the sensor curved such that the one main face has a recessed shape.

As illustrated in FIG. 4B, when the sensor 10 is curved such that the one main face on the side where the electrode base 11 is provided has a recessed shape, the electrode base 13 deforms such that the recessed bend of the shaped portion 13b is gentle or the shaped portion 13b is substantially flat. On the other hand, the electrode base 11 deforms such that the recessed bend of the shaped portion 11b is further increased or the shaped portion 11b is pressed against the one main face of the sensor electrode layer 20. With this arrangement, the shear stress acting between the electrode base 11 and the deformable layer 12 and between the electrode base 13 and the deformable layer 14 can be reduced.

[Operation of Sensor]

Next, the operation of the sensor 10 according to the first embodiment of the present technology will be described. Here, the operation of the sensor 10 will be described in a case where the sensor 10 is worn on a subject body such that the other main face of the sensor 10 is opposed to the subject body (for example, a human body, an object, or the like).

When the controller IC 33 applies a voltage between the pulse electrode 22 and the sense electrodes 23, that is, between the sub-electrodes 22c and 23c, electric lines of force (capacitive coupling) are formed between the sub-electrodes 22c and 23c.

When pressure is applied to the one main face of the sensor 10, the deformable layers 12 and 14 deform elastically, the electrode base 11 bends toward the sensor electrode layer 20, and the sensor electrode layer 20 bends toward the electrode base 13. As a result, the electrode base 11 approaches the sensor electrode layer 20, and the sensor electrode layer 20 approaches the electrode base 13. Thus, part of the electric lines of force between the sub-electrodes 22c and 23c flows into the electrode bases 11 and 13 to change the electrostatic capacity of each sensing unit 20s. The controller IC 33 detects the pressure applied to the one main face of the sensor 10, on the basis of the change in the electrostatic capacity, and outputs the result to the CPU 34.

In the description of the operation of the sensor 10 described above, the case where the pressure applied to the one main face of the sensor 10 is detected has been described. However, pressure applied to the other main face of the sensor 10 can also be detected. In a case where the subject body is part of a human body such as a wrist, the CPU 34 is capable of detecting pulse, heartbeat, or the like, on the basis of the pressure applied to the other main face of the sensor 10.

[Effects]

For the sensor 10 according to the first embodiment, the deformable layers 12 and 14 are discontinuous between the sensing units 20s, and the electrode bases 11 and 13 have the shaped portions 11b and 13b, respectively between the sensing units 20s. Thus, the deformable layers 12 and 14 easily deform between the sensing units 20s. Therefore, the shear stress acting between the electrode base 11 and the deformable layer 12 and between the electrode base 13 and the deformable layer 14 when the sensor 10 is bent is reduced, and occurrence of separation between the electrode base 11 and the deformable layer 12 and between the electrode base 13 and the deformable layer 14 can be suppressed. As a result, the sensor 10 that is flexible and high in bending durability can be obtained.

Furthermore, on each sensing unit 20s, the distance between the electrode base 11 and the sensor electrode layer 20 and the distance between the electrode base 13 and the sensor electrode layer 20 are held by the deformable layers 12 and 14, respectively. Thus, decrease in the sensitivity of the sensing unit 20s can be suppressed. Therefore, the flexibility of the sensor 10 can be secured while maintaining the high sensitivity and high accuracy of the sensor 10. Furthermore, increase in the initial output resulting from decrease in the distance between the electrode base 11 and the sensor electrode layer 20 and the distance between the electrode base 13 and the sensor electrode layer 20 can also be suppressed. Note that, as a technology for obtaining an effect similar to that of the sensor 10 according to the first embodiment, it is conceivable that a REF electrode layer and a base included in an electrode base each include a stretchable material. However, such a stretchable electrode material has concerns for the durability, so that the configuration of the sensor 10 according to the first embodiment is more effective.

MODIFIED EXAMPLES

Figure 5A:
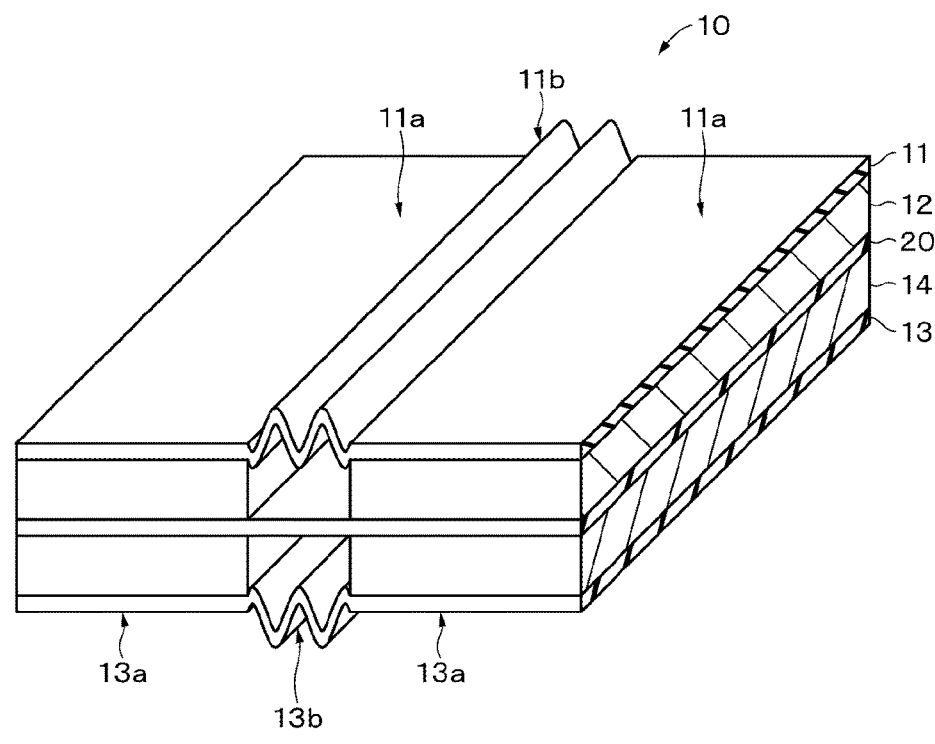
FIG. 5A is a perspective view illustrating a modified example of a shaped portion.

The sensor 10 may be provided with only the REF electrode layers 11d and 13d instead of the electrode bases 11 and 13. The electrode bases 11 and 13 may be provided with extensible and contractible shaped portions 11b and 13b, respectively. For example, as illustrated in FIG. 5A, the electrode bases 11 and 13 may have corrugated shaped portions 11b and 13b, respectively.

Figure 5B:
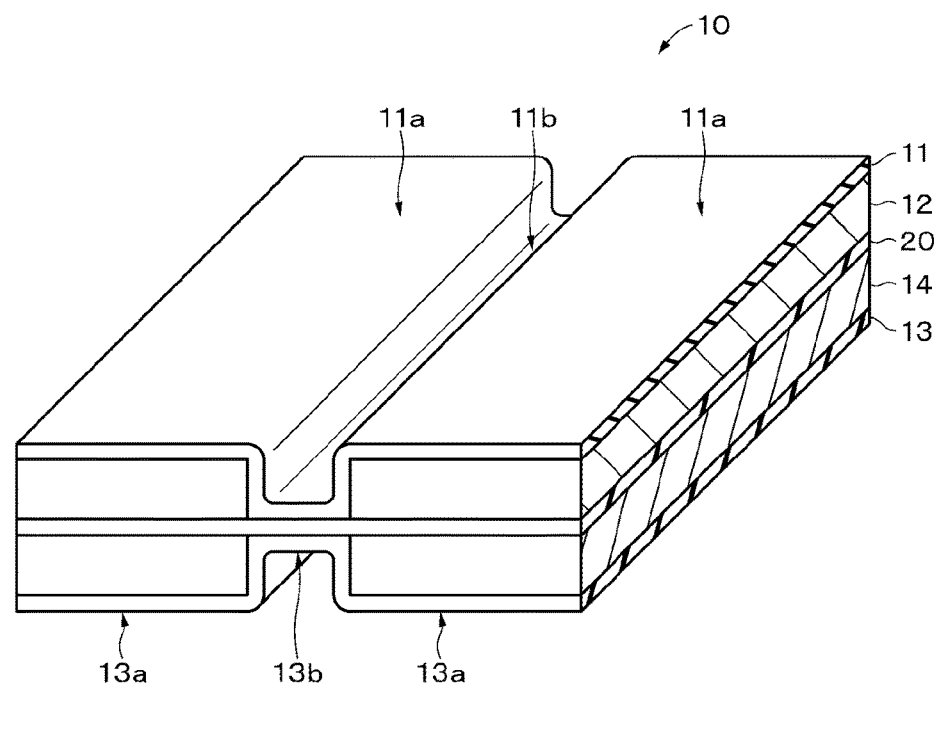
FIG. 5B is a perspective view illustrating a modified example of the shaped portion.

As illustrated in FIG. 5B, between the adjacent deformable layers 12, the shaped portion 11b may be in close contact with the one main face of the sensor electrode layer 20. Furthermore, between the adjacent deformable layers 14, the shaped portion 13b may be in close contact with the other main face of the sensor electrode layer 20. In this case, the close-contact shaped portion 11b may be stuck to the one main face of the sensor electrode layer 20, and the close-contact shaped portion 13b may be stuck to the other main face of the sensor electrode layer 20. The electrode bases 11 and 13 having the above-described shaped portions 11b and 13b, respectively can be formed by, for example, hot press molding.

In the above-described configuration, the respective bottoms of the shaped portions 11b and 13b and the sensor electrode layer 20 are substantially equal in curvature. Therefore, even in a case where a configuration in which the shaped portions 11b and 13b are stuck to the sensor electrode layer 20 is adopted, the shear stress acting between the layers of the sensor 10 when the sensor 10 is bent can be reduced. Furthermore, in the case where the configuration in which the shaped portions 11b and 13b are stuck to the sensor electrode layer 20 is adopted, the stability of the sensor 10 as a product can be improved.

Figure 6A:
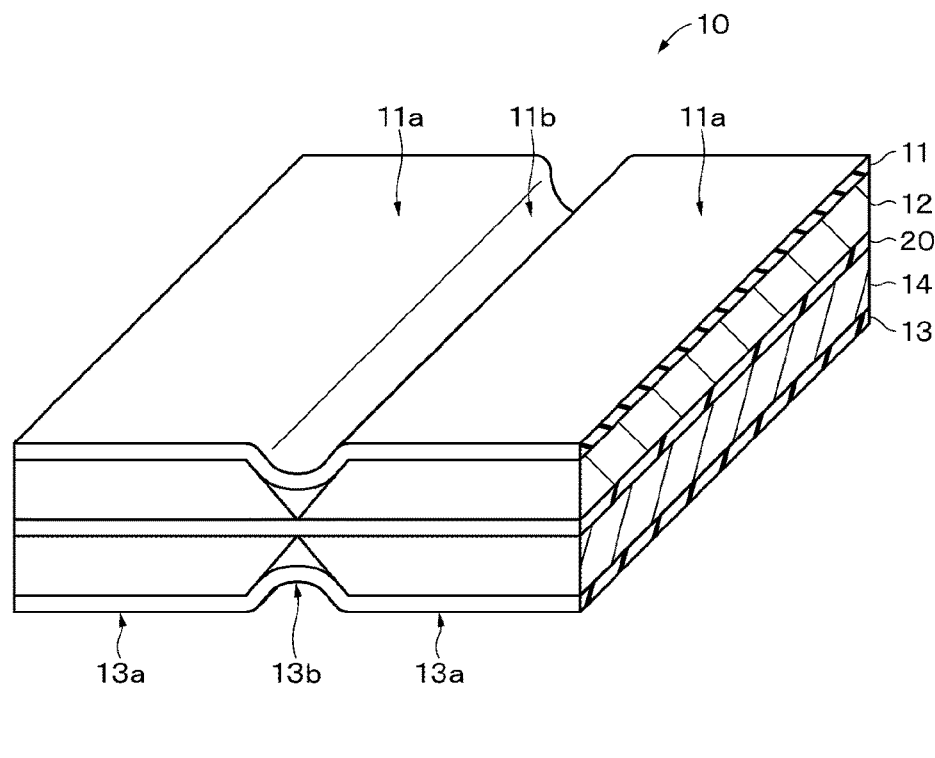
FIG. 6A is a perspective view illustrating a modified example of the shaped portion.

As illustrated in FIG. 6A, respective side faces of the deformable layers 12 between the adjacent deformable layers 12 and respective side faces of the deformable layers 14 between the adjacent deformable layers 14 may each have an inclined face such the deformable layers 12 and 14 each gradually decrease in thickness, a curved face, or a step-like shape.

Figure 6B:
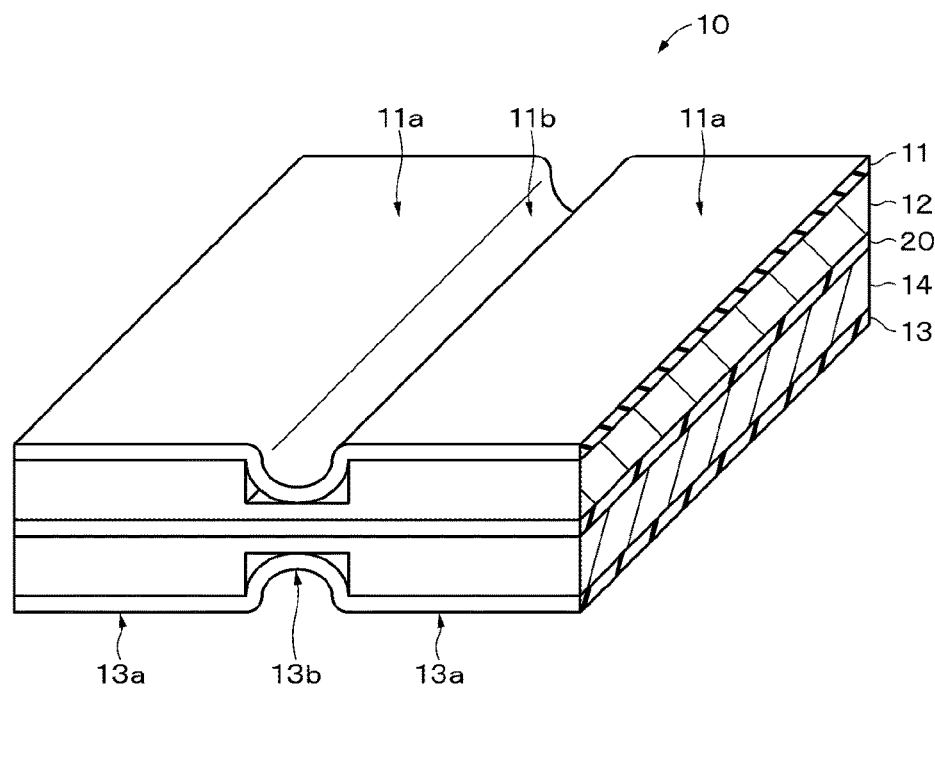
FIG. 6B is a perspective view illustrating a modified example of the shaped portion.

As illustrated in FIG. 6B, instead of the configuration in which the deformable layers 12 and 14 are discontinuous between the sensing units 20s, the deformable layers 12 and 14 may be recessed toward the main faces of the sensor electrode layer 20 between the sensing units 20s.

Figure 7:
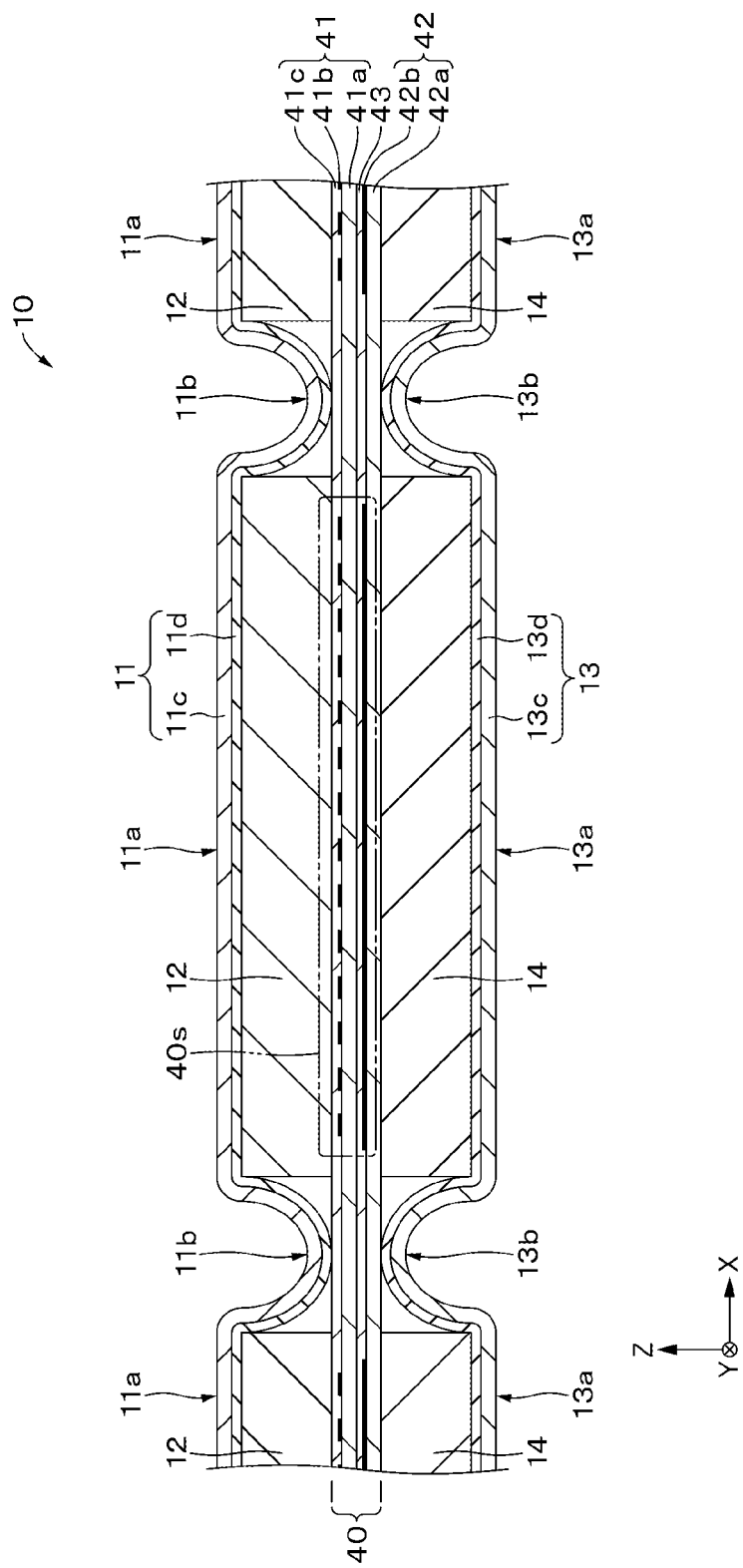
FIG. 7 is a perspective view illustrating a modified example of the sensor electrode layer.

As illustrated in FIG. 7, instead of the sensor electrode layer 20, the sensor 10 may be provided with a sensor electrode layer 40 obtained by sticking together two electrode bases 41 and 42 via an adhesive layer 43. The electrode base 41 includes a base 41a, one pulse electrode 41b provided on one main face of the base 41a, and an insulating layer 41c covering the pulse electrode 41b. The electrode base 42 includes a base 42a and a plurality of sense electrodes 42b provided on one main face of the base 42a. The adhesive layer 43 sticks together another main face of the base 41a and the one main face of the base 42a. A sensing unit 40s includes the pulse electrode 41b and a sense electrode 42b overlapping each other in the thickness direction (Z-axis direction) of the sensor 10.

Figure 8A:
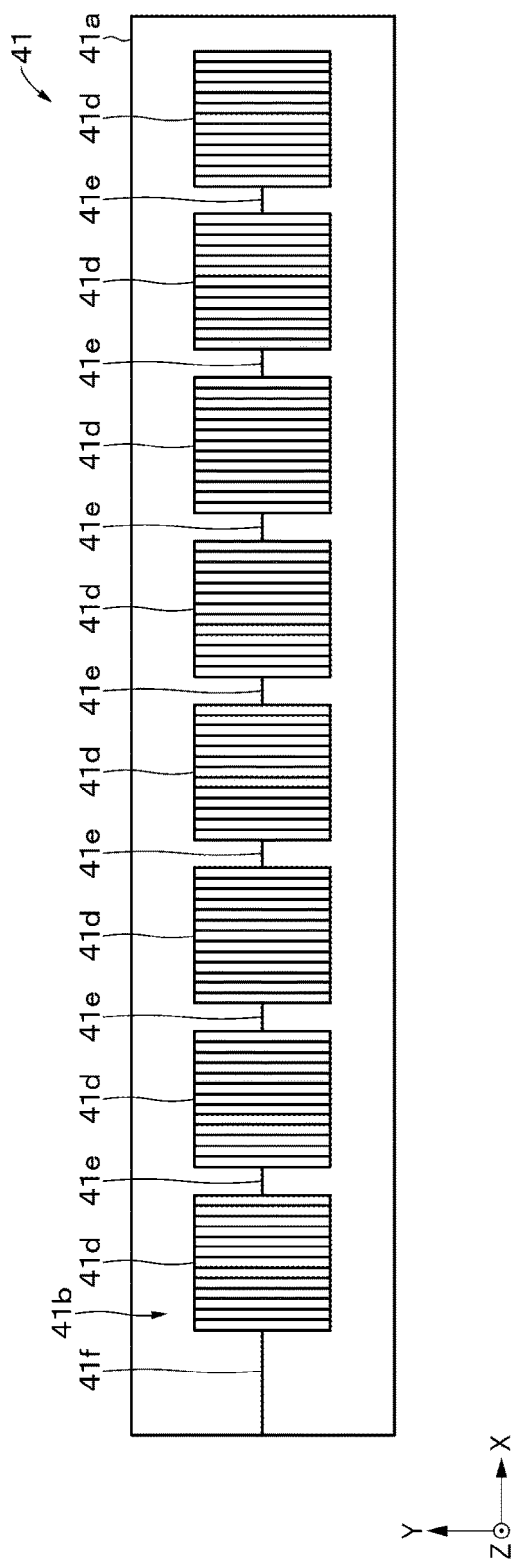
FIG. 8A is a plan view illustrating the configuration of an electrode base having a pulse electrode.
Figure 8B:
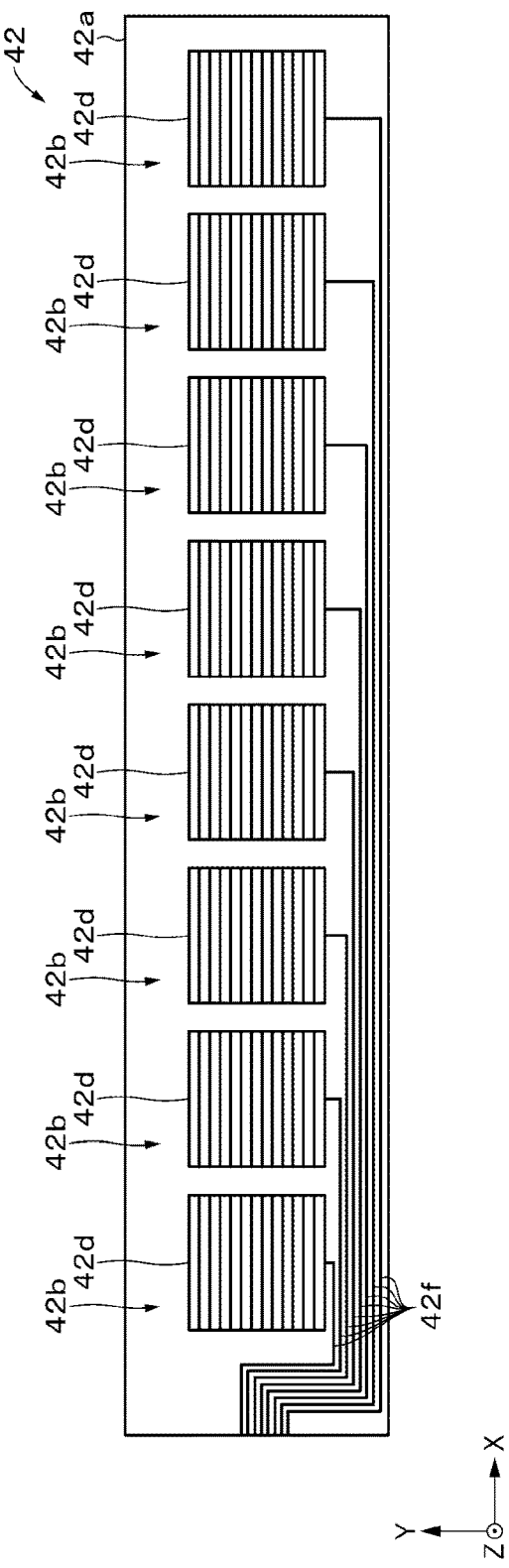
FIG. 8B is a plan view illustrating the configuration of an electrode base having sense electrodes.

As illustrated in FIG. 8A, the pulse electrode 41b includes a plurality of unit electrode bodies 41d and a plurality of connection portions 41e. The plurality of unit electrode bodies 41d is one-dimensionally disposed forming one array at constant intervals in the X-axis direction, and the unit electrode bodies 41d adjacent to each other are connected by the connection portions 42e. As illustrated in FIG. 8B, each sense electrode 42b includes one unit electrode body 43a. The respective unit electrode bodies 43a of the plurality of sense electrodes 42b are one-dimensionally disposed forming one array at constant intervals in the X-axis direction.

A wiring 41f is drawn out from one end of the pulse electrode 41b and connected to the FPC 31. A wiring 42f is also drawn out from one end of each sense electrode 42b, routed around the peripheral portion of the one main face of the base 21, and connected to the FPC 31.

Examples of the shape of the unit electrode bodies 41d and 42d include, but are not limited to, a flat plate shape, a net shape, a stripe shape, a concentric shape, a spiral shape, a radial shape, a stripe shape, and the like. The sensing unit 40s includes the unit electrode bodies 41d and 42d overlapping each other in the thickness direction (Z-axis direction) of the sensor electrode layer 20.

Figure 9:
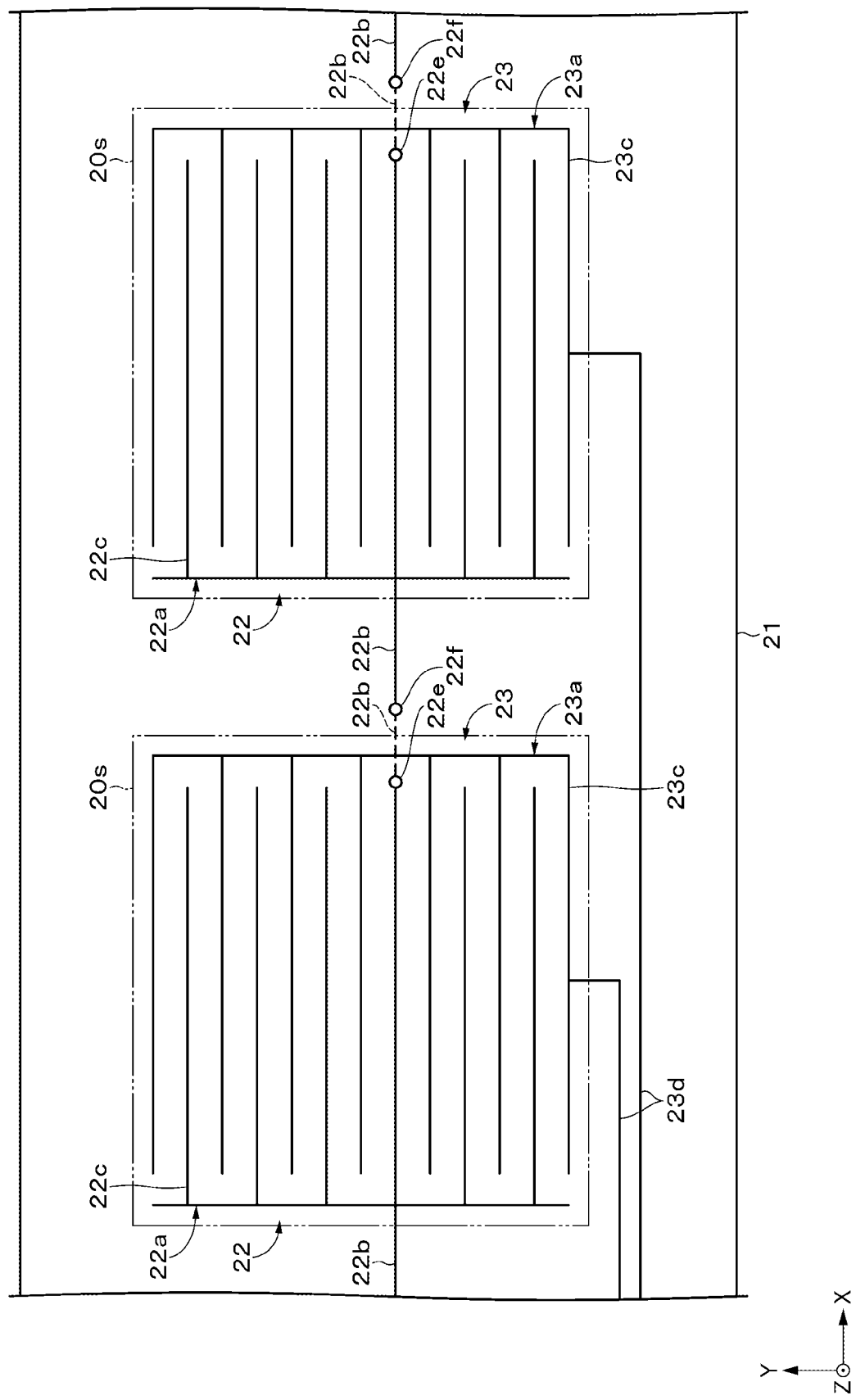
FIG. 9 is a perspective view illustrating a modified example of the sensor electrode layer.

As illustrated in FIG. 9, the unit electrode bodies 22a and 23a may each have a comb-teeth shape in which the plurality of sub-electrodes 22c or the plurality of sub-electrodes 23c extends in the X-axis direction. Furthermore, the base 21 may have via holes 22e and 22f as through holes. In this case, each connection portion 22b is routed from the one main face to another main face of the base 21 via the via hole 22e, returned from the other main face to the one main face of the base 21 via the via hole 22f, so that the unit electrode bodies 22a adjacent each other are connected together. With this arrangement, the adjacent unit electrode bodies 22a can be connected together without a jumper wiring or the like.

Figure 10:
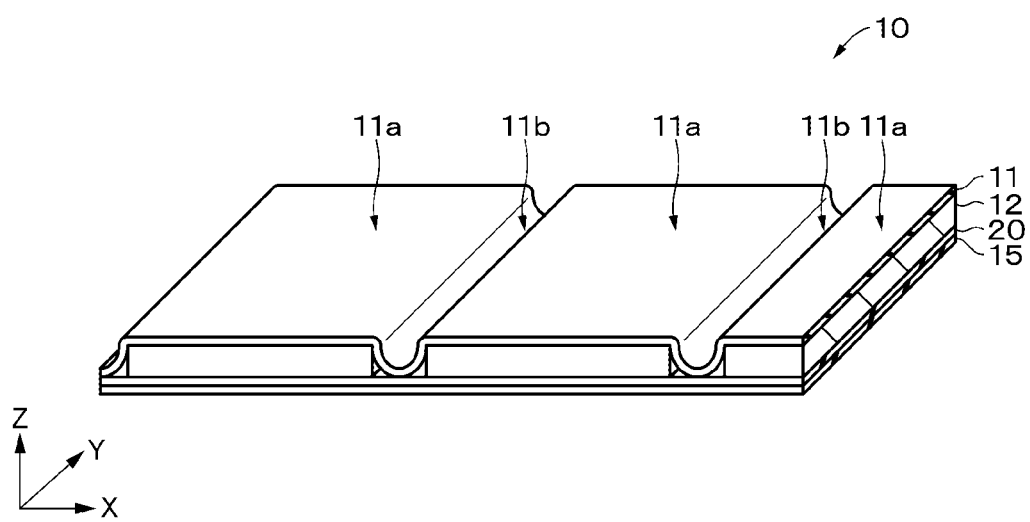
FIG. 10 is a perspective view illustrating a modified example of the sensor.

As illustrated in FIG. 10, the sensor 10 may not include the deformable layer 14 on the other main face side of the sensor 10, and the sensor 10 and an electrode base 15 may be provided adjacent to each other. In this case, the sensor 10 is stuck to the electrode base 15 via an adhesive layer (not illustrated). The electrode base 15 is similar to the electrode base 13 except that the electrode base 15 has no shaped portion 13b and has a flat shape as a whole.

The sensor electrode layer 20 and the deformable layers 12 and 14 may have stretchability. The electrode bases 11 and 13 have the shaped portions 11b and 13b, respectively, whereby the electrode bases 11 and 13 can be easily extended and contracted in the in-plane direction of the sensor 10. Thus, if the sensor electrode layer 20 and the deformable layers 12 and 14 have stretchability, the stretchability of the entire sensor 10 can be obtained. As a result, the sensor 10 having higher bending durability can be obtained.

An FPC may be used as the base 21 of the sensor electrode layer 20. In this case, the sensor electrode layer 20 can be directly connected to the PCBA 32 without the FPC 31, so that the impact durability of the connection between the sensor 10 and the PCBA 32 is improved.

2 Second Embodiment

[Configuration of Sensor]

Figures 11A, 11B:
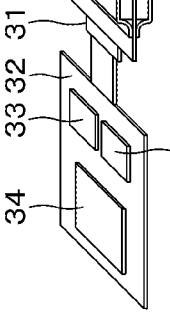
FIG. 11A is a perspective view illustrating the configuration of a sensor according to a second embodiment of the present technology.
FIG. 11B is a cross-sectional view taken along line XIB-XIB in FIG. 11A.

As illustrated in FIG. 11A, a sensor 10A according to a second embodiment of the present technology includes, on one main face of the sensor 10A, a first region R1 functioning as a pressure-sensitive sensor, and a second region R2 functioning as both of a pressure-sensitive sensor and an electrostatic-capacity-type touch sensor. Note that, in the second embodiment, parts similar to those of the first embodiment are denoted by the same reference numerals, and description thereof is omitted.

The sensor 10A detects electrostatic capacity corresponding to pressure applied to the first region R1, and outputs an output signal corresponding to the detected electrostatic capacity to a controller IC 33. Furthermore, the sensor 10A detects electrostatic capacity corresponding to pressure applied to the second region R2 or electrostatic capacity corresponding to touch at zero force on the second region R2, and outputs an output signal corresponding to the electrostatic capacity to a controller IC 35.

The sensor 10A has a configuration similar to that of the sensor 10 according to the above-described first embodiment (see FIG. 2), in the first region R1. On the other hand, in the second region R2, as illustrated in FIG. 11B, the sensor 10A includes only a base 11c instead of the electrode base 11. Thus, a REF electrode layer 11d is provided in the first region R1 between the first and second regions R1 and R2, and opposed to part of one main face of a sensor electrode layer 20.

Figure 12:
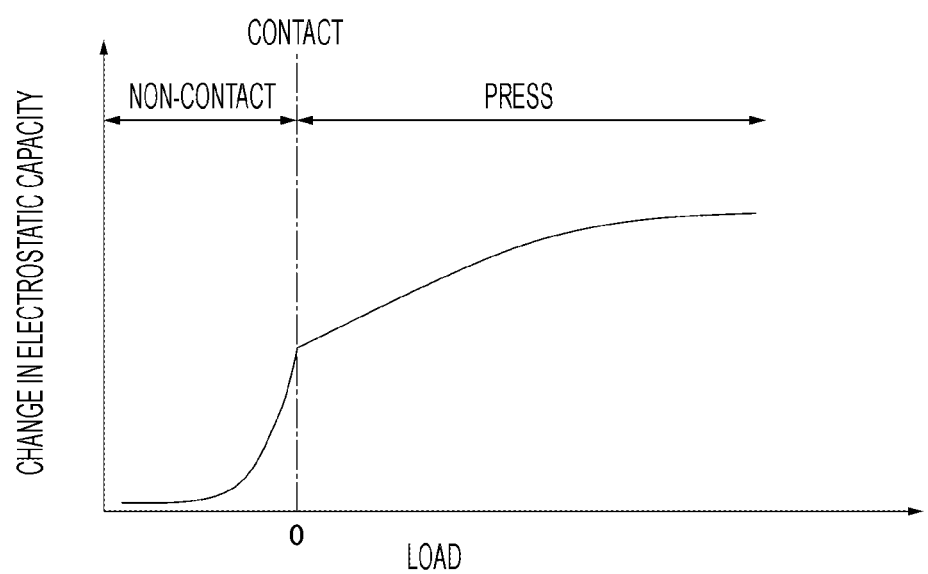
FIG. 12 is a graph illustrating a change in electrostatic capacity when a conductor such as a finger approaches a second region R2 and then presses the second region R2.

FIG. 12 illustrates a change in electrostatic capacity when a conductor such as a finger approaches the second region R2 and then presses the second region R2. For the sensor 10A having the above-described configuration, when the conductor such as the finger approaches or contacts the second region R2, part of electric lines of force between sub-electrodes 22c and 23c flows into the conductor to rapidly change the electrostatic capacity of each sensing unit 20s. The controller IC 35 detects, on the basis of the change in the electrostatic capacity, that a touch operation has been performed on the second region R2, and outputs the detection result to a CPU 34.

When the second region R2 is pressed with the conductor such as the finger, the conductor approaches the sensor electrode layer 20, and the sensor electrode layer 20 approaches an electrode base 13. As a result, part of the electric lines of force between the sub-electrodes 22c and 23c further flows into the conductor and part of the electric lines of force between the sub-electrodes 22c and 23c also flows into the electrode base 13 to further change the electrostatic capacity of each sensing unit 20s. The controller IC 35 detects the pressure applied to the second region R2, on the basis of the change in the electrostatic capacity, and outputs the detection result to the CPU 34.

[Effects]

The sensor 10A according to the second embodiment includes, on the one main face of the sensor 10A, the first region R1 functioning as a pressure-sensitive sensor and the second region R2 functioning as both of a pressure-sensitive sensor and an electrostatic-capacity-type touch sensor. With this arrangement, various input operations can be performed with one sensor 10A.

Modified Examples

In the above-described second embodiment, the configuration in which part of the region in the one main face of the sensor 10A is the second region R2 has been described. However, the entire one main face of the sensor 10A may be the second region R2. In other words, the sensor 10A may include only the base 11c instead of the electrode base 11. In a case where such a configuration is adopted, both of zero-force touch detection and pressure detection can be performed on the entire one main face of the sensor 10A.

Furthermore, the sensor 10A may include the first region R1 and the second region R2 on both main faces of the sensor 10A, or only the second region R2 may be provided on both main faces of the sensor 10A.

3 Third Embodiment

[Configuration of Sensor]

Figure 13A:
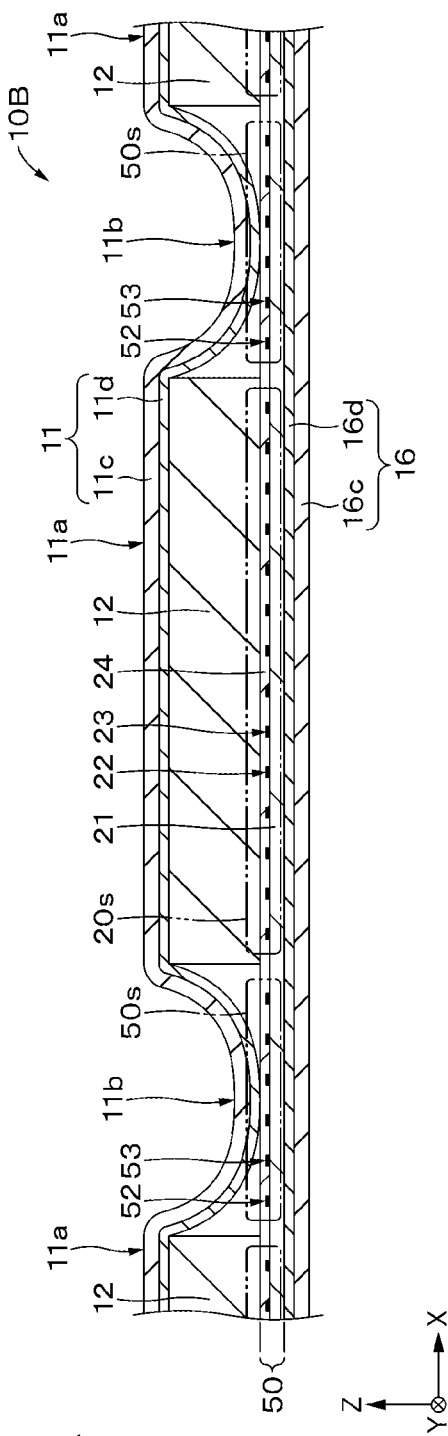
FIG. 13A is a cross-sectional view illustrating the configuration of a sensor according to a third embodiment of the present technology.

For a sensor 10B according to a third embodiment of the present technology, as illustrated in FIG. 13A, a sensor electrode layer 50 further includes a sensing unit 50s between sensing units 20s. Furthermore, the sensor 10B includes no deformable layer 14 on the other main face side of a sensor 10, and the sensor 10 and an electrode base 16 are provided adjacent to each other. Note that, in the third embodiment, parts similar to those in the first embodiment are denoted by the same reference numerals, and description thereof is omitted.

The sensor electrode layer 50 includes one pulse electrode 52 and a plurality of sense electrodes 53 provided on one main face of a base 21. The sensing unit 50s includes the pulse electrode 52 and a sense electrode 53. With the plurality of sensing units 20s in plan view in the Z-axis direction, the sensing units 20s and 50s are alternately disposed in the X-axis direction.

Figure 13B:
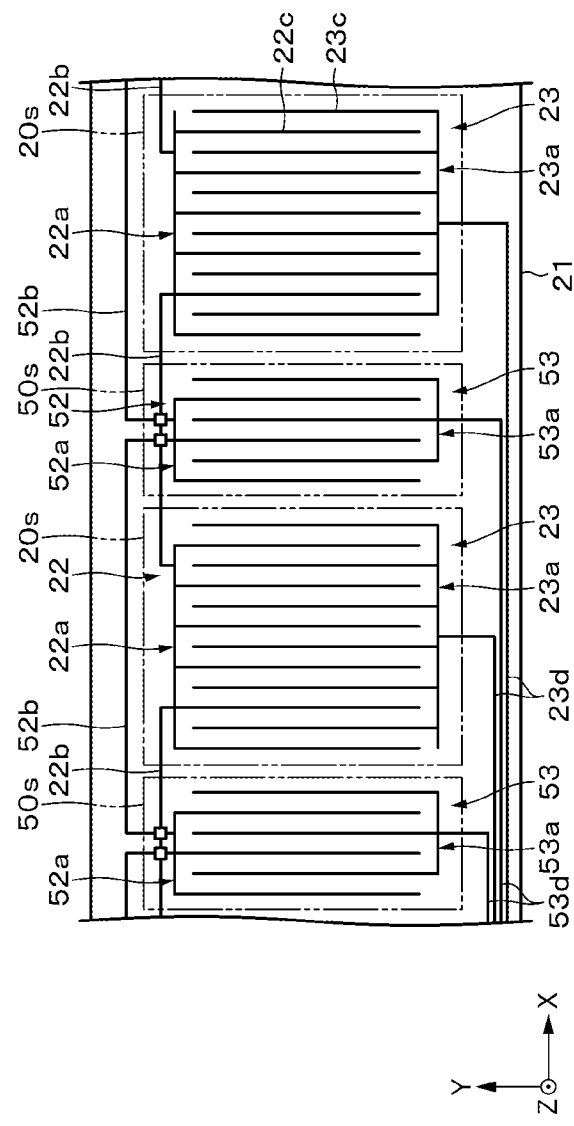
FIG. 13B is a plan view illustrating the configuration of a sensor electrode layer.

As illustrated in FIG. 13B, the pulse electrode 52 as a third electrode includes a plurality of unit electrode bodies 52a and a plurality of connection portions 52b. The plurality of unit electrode bodies 52a is one-dimensionally disposed forming one array at constant intervals in the X-axis direction, and the unit electrode bodies 52a adjacent to each other are connected by the connection portions 52b. As illustrated in FIG. 13B, each sense electrode 53 as a fourth electrode includes one unit electrode body 53a. The respective unit electrode bodies 53a included in the plurality of sense electrodes 53 are one-dimensionally disposed forming one array at constant intervals in the X-axis direction.

A wiring (not illustrated) is drawn out from one end of the pulse electrode 52 and connected to an FPC 31. A wiring 53d is also drawn out from one end of each sense electrode 53, routed around the peripheral portion of the one main face of the base 21, and connected to the FPC 31.

The unit electrode bodies 52a have a configuration similar to that of the unit electrode bodies 22a and the unit electrode bodies 53a have a configuration similar to that of the unit electrode bodies 23a in the first embodiment.

The electrode base 16 is similar to the electrode base 13 except that the electrode base 16 has no shaped portion 13b and includes a base 16c and a REF electrode layer 16d in flat shape as a whole.

[Operation of Sensor]

When the sensor 10 is curved such that the one main face on the side where an electrode base 11 is provided has a protruding shape, the electrode base 11 deforms such that the recessed bend of a shaped portion 11b is gentle or the shaped portion 11b is substantially flat. As a result, the shaped portion 11b is far from the sensing unit 50s, and the electrostatic capacity of the sensing unit 50s increases.

On the other hand, when the sensor 10 is curved such that the one main face on the side where the electrode base 11 is provided has a recessed shape, the electrode base 11 deforms such that the recessed bend of the shaped portion 11b is further increased or the shaped portion 11b is pressed against one main face of a sensor electrode layer 20. As a result, the shaped portion 11b comes close to the sensing unit 50s, and the electrostatic capacity of the sensing unit 50s decreases.

On the basis of the electrostatic capacity supplied from the sensing unit 50s, a controller IC 33 detects the curving or the degree of curving of the sensor 10B. On the basis of the detection result of the curving or the degree of curving, the controller IC 33 may correct an electrostatic capacity distribution (that is, pressure distribution) detected by each sensing unit 20s or may estimate the context. Note that a controller that detects the curving or the degree of curving may be provided separately from the controller IC 33.

[Effects]

For the sensor 10B according to the third embodiment, the sensor electrode layer 50 further includes the sensing unit 50s between the sensing units 20s, so that bending of the sensor 10B can be detected.

Modified Examples

The sensor electrode layer 20 and a deformable layer 12 may each include an extensible and contractible material, and the entire sensor 10A may be extensible and contractible. In this case, when the sensor 10A is extended, the shaped portion 11b is far from the sensing unit 50s, whereby the electrostatic capacity of the sensing unit 50s decreases. On the other hand, when the sensor 10A is contracted, the shaped portion 11b comes close to the sensing unit 50s, and the electrostatic capacity of the sensing unit 50s increases. Therefore, on the basis of the electrostatic capacity supplied from the sensing unit 50s, the controller IC 33 can detect extension and contraction of the sensor 10B.

The sensor 10B may include an electrode base 13 instead of the electrode base 16 and may include a deformable layer 14 may be provided between the electrode base 13 and the sensor electrode layer 20. In this case, it is preferable that the shaped portion 11b has a shape following a shape between the deformable layers 12 and a deformable layer 12 adjacent thereto, and a shaped portion 13b also has a shape following a shape between the deformable layer 14 and a deformable layer 14 adjacent thereto. This is because the change in the electrostatic capacity detected by the sensing unit 50s is larger when the sensor 10B is curved and the detection precision for the curving is improved.

4 Fourth Embodiment

[Configuration of Sensor]

Figure 14A:
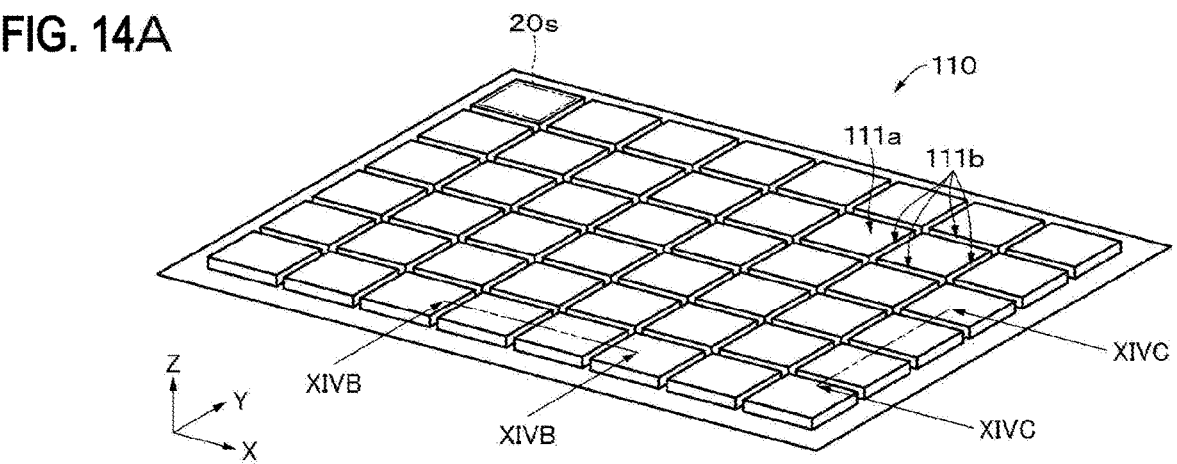
FIG. 14A is a perspective view illustrating the configuration of a sensor according to a fourth embodiment of the present technology.
Figure 14B:
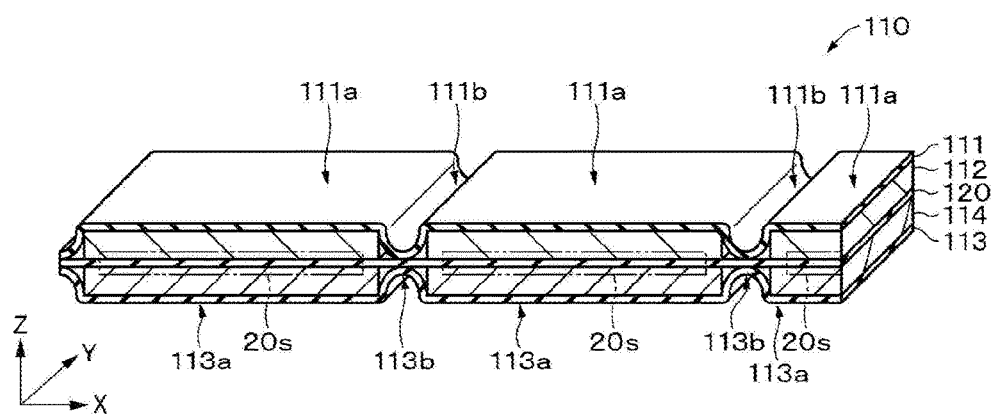
FIG. 14B is a cross-sectional view taken along line XIVB-XIVB in FIG. 14A.
Figure 14C:
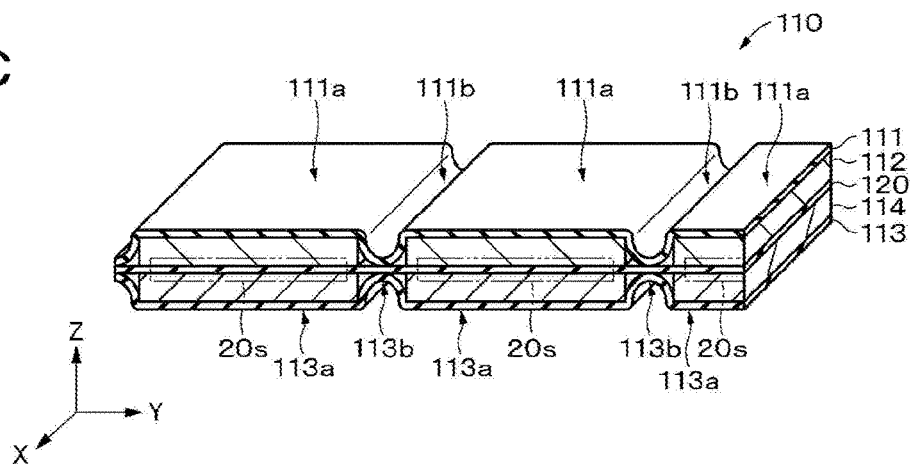
FIG. 14C is a cross-sectional view taken along line XIVC-XIVC in FIG. 14A.

As illustrating in FIG. 14A, a sensor 110 according to a fourth embodiment of the present technology has a rectangular sheet shape, and sensing units 20s are disposed two-dimensionally in the in-plane direction of the sensor 110. As illustrated in FIGS. 14B and 14C, the sensor 110 includes an electrostatic-capacity-type sensor electrode layer 120, electrode bases 111 and 113, and deformable layers 112 and 114. Note that, in this specification, axes orthogonal to each other in the plane of the sensor 110 in a flat state each are referred to as the X-axis and the Y-axis, and an axis perpendicular to both of the −X axis and the −Y axis is referred to as the Z-axis.

The sensor electrode layer 120, the electrode bases 111 and 113, and the deformable layers 112 and 114 included in the sensor 110 will be sequentially described below.

(Sensor Electrode Layer)

The sensor electrode layer 120 includes the plurality of sensing units 20s. The plurality of sensing units 20s is disposed two-dimensionally in a matrix in a state where a sensor electrode layer 20 is flat.

(Electrode Base)

Each electrode base 111 includes an opposed portion 111a opposed to the sensing unit 20s and a shaped portion 111b provided between the opposed portion 111a and an opposed portion 111a. Each electrode base 113 includes an opposed portion 113a opposed to the sensing unit 20s and a shaped portion 113b provided between the opposed portion 113a and an opposed portion 113a. With the sensor 110 in plan view in a direction perpendicular to one main face of the sensor 110 (Z-axis direction), the opposed portions 111a and 113a and the sensing unit 20s are disposed two-dimensionally in a matrix overlapping each other in the thickness direction (Z-axis direction) of the sensor 110. The shaped portions 111b and 113b are provided between the adjacent opposed portions 11a in the X-axis direction and the Y-axis direction.

(Deformable Layer)

Each deformable layer 112 is intermittently provided being discontinuous between the adjacent sensing units 20s in the X-axis direction and the Y-axis direction. Specifically, the deformable layer 112 is disposed two-dimensionally in a matrix overlapping with the sensing unit 20s in the thickness direction (Z-axis direction) of the sensor 10, and a space is provided between the deformable layers 112 adjacent thereto in the X-axis direction and the Y-axis direction. The deformable layer 112 is interposed between one main face of the sensor electrode layer 120 and the opposed portion 111a, and the shaped portion 111b is disposed in the space between the adjacent deformable layers 112 in the X-axis direction and the Y-axis direction.

Each deformable layer 114 is intermittently provided being discontinuous between the adjacent sensing units 20s in the X-axis direction and the Y-axis direction. Specifically, the deformable layer 114 is disposed two-dimensionally in a matrix overlapping with the sensing unit 20s in the thickness direction (Z-axis direction) of the sensor 10, and a space is provided between the deformable layers 114 adjacent thereto in the X-axis direction and the Y-axis direction. The deformable layer 114 is interposed between another main face of the sensor electrode layer 120 and the opposed portion 113a, and the shaped portion 113b is disposed in the space between the adjacent deformable layers 114 in the X-axis direction and the Y-axis direction.

[Effects]

Even in a case where the sensor 110 according to the fourth embodiment is repeatedly worn on a subject body or the like having a three-dimensional surface, occurrence of separation between the electrode base 111 and the deformable layer 112 and between the electrode base 113 and the deformable layer 114 can be suppressed. As a result, the sensor 110 that is flexible and high in bending durability can be obtained.

5 Fifth Embodiment

In a fifth embodiment, as an example of a battery device attachable to and detachable from a human body, a wristwatch-type electronic device including the sensor 10 according to the first embodiment in a band will be described.

[Configuration of Wristwatch-Type Electronic Device]

Figure 15A:
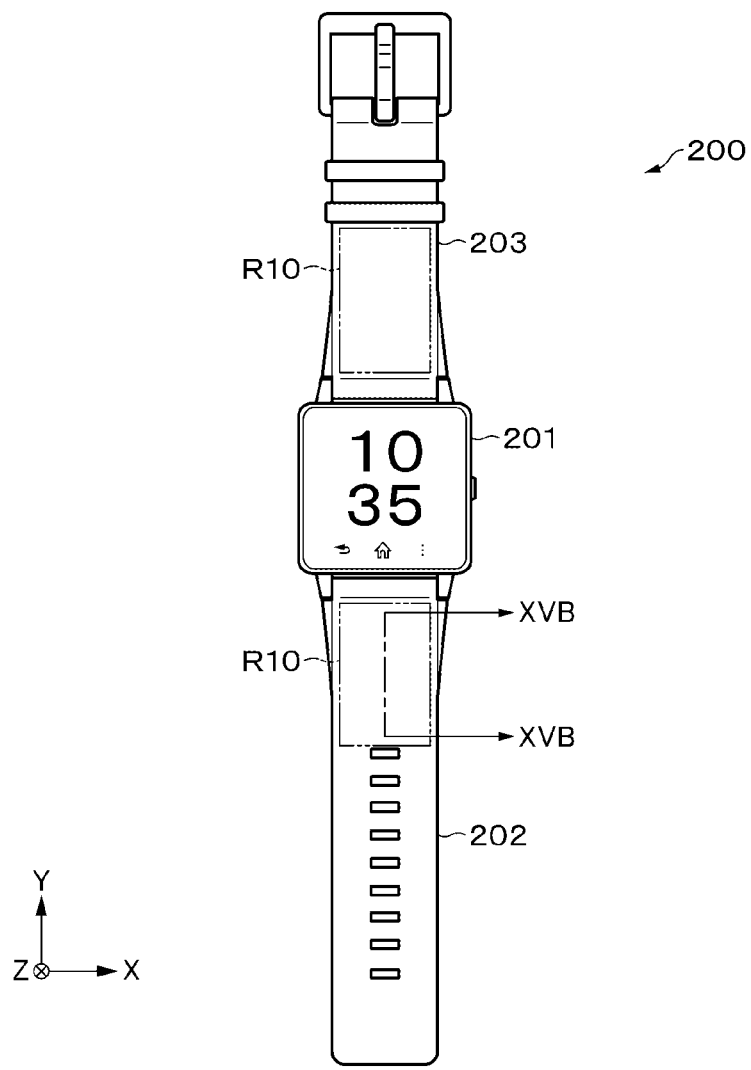
FIG. 15A is a plan view illustrating the external appearance of a wristwatch-type electronic device according to a fifth embodiment of the present technology.

As illustrated in FIG. 15A, a wristwatch-type electronic device 200 according to the fifth embodiment of the present technology includes a main body unit 201 of the wristwatch-type electronic device 200, bands 202 and 203 attached to the main body unit 201. The bands 202 and 203 may be attachable to and detachable from the main body unit 201 such that the user can replace the bands 202 and 203. The band 202 has an operation area R10 on one main face of the band 202. The sensor 10 according to the first embodiment is provided inside the operation area R10. Note that the band 203 may also have the operation area R10.

Figure 15B:
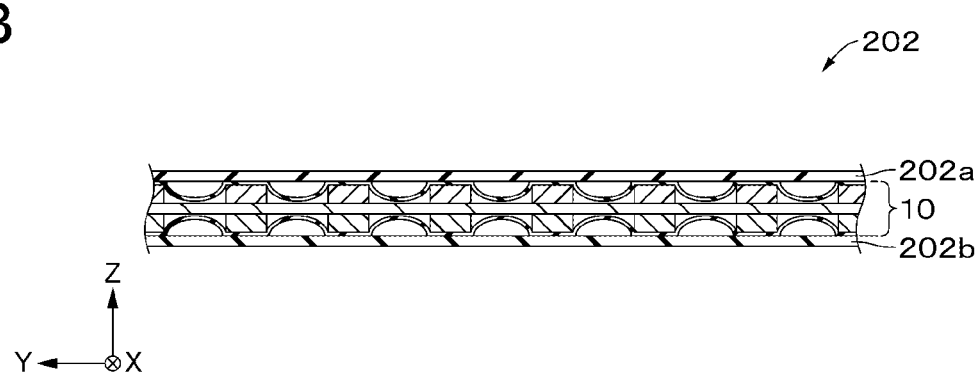
FIG. 15B is a cross-sectional view taken along line XVB-XVB in FIG. 15A.

As illustrated in FIG. 15B, the band 202 includes the sensor 10, a film-shaped exterior member 202a provided on the one main face of the sensor 10, a film-shaped exterior member 202b provided on the other main face of the sensor 10.

[Configuration of Main Body Unit]

Figure 16:
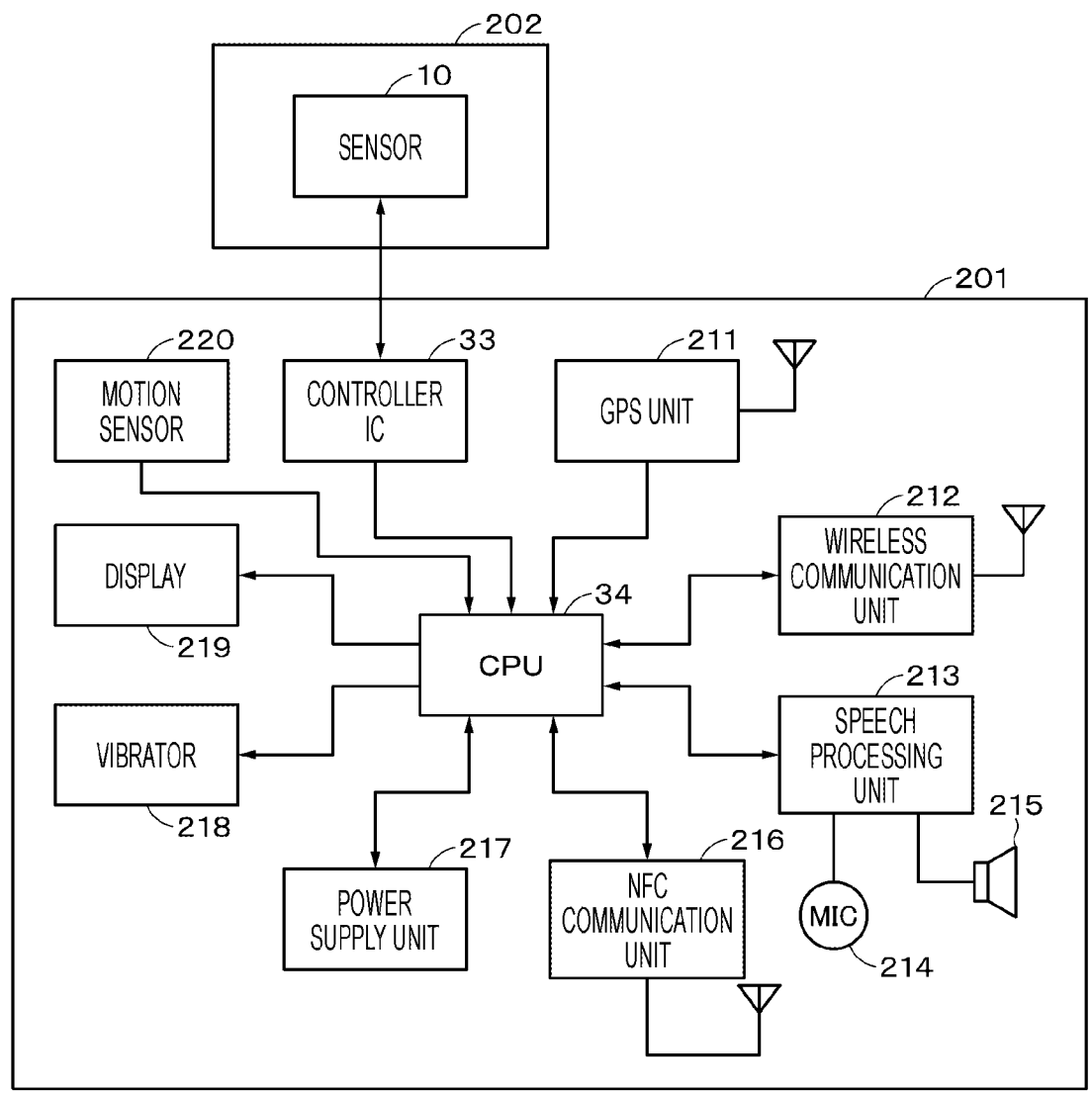
FIG. 16 is a block diagram illustrating the circuit configuration of a main body portion of the wristwatch-type electronic device.

As illustrated in FIG. 16, the main body unit 201 includes a CPU 34, a controller IC 33, a GPS unit 211, a wireless communication unit 212, a speech processing unit 213, a microphone 214, a speaker 215, an NFC communication unit 216, a power supply unit 217, a vibrator 218, a display 219, and a motion sensor 220. As illustrated in FIG. 1, the sensor 10 is connected to the controller IC 33 via the FPC 31. Note that the bands 202 and 203 may be provided with one of an NFC communication unit, a battery, a vibrator, or the like.

The GPS unit 211 is a positioning unit that receives a radio wave from a satellite of a system called global positioning system (GPS) and performs positioning of the current position. The wireless communication unit 212 performs near field communication with other terminals under the Bluetooth (registered trademark) standard, for example. The NFC communication unit 216 performs wireless communication with a close reader/writer under the near field communication (NFC) standard. Data obtained by the GPS unit 211, the wireless communication unit 212, and the NFC communication unit 216 is supplied to the CPU 34.

The microphone 214 and the speaker 215 are connected to the speech processing unit 213, and the speech processing unit 213 performs processing of a call with a party connected by wireless communication at the wireless communication unit 212. Furthermore, the speech processing unit 213 is also capable of performing processing for a speech input operation.

The power supply unit 217 supplies power to the CPU 34, the display 219, and the like provided in the main body unit 201. The power supply unit 217 includes a secondary battery such as a lithium ion secondary battery, a charge and discharge control circuit that controls charging and discharging of the secondary battery, and the like. Note that, although not illustrated in FIG. 16, the main body unit 201 includes a terminal for charging the secondary battery.

The vibrator 218 is a member that vibrates the main body unit 201. For example, the wristwatch-type electronic device 200 vibrates the main body unit 201 with the vibrator 218, and issues a notification for reception of a telephone call, reception of an E-mail, or the like.

The display 219 is a liquid crystal display, an electroluminescence (EL) display, or the like. The display 219 displays information such as characters, numeric characters, images, for example, various types of information such as time, reception of a telephone call, and reception of an E-mail.

The motion sensor 220 detects a movement of the user wearing the wristwatch-type electronic device 200. Examples of the motion sensor 220 that is used include, an accelerometer, a gyro sensor, an electronic compass, a barometric pressure sensor, and the like.

The sensor 10 is a pressure sensor with high sensitivity and high position resolution, detects electrostatic capacity corresponding to a pressing operation on the operation area R10, and outputs an output signal corresponding to the electrostatic capacity to the controller IC 33.

On the basis of the output signal supplied from the sensor 10, the controller IC 33 serving as a driving IC detects the pressing operation on the operation area R10 of the band 202, and issues a notification for the detection result to the CPU 34. Note that, as the controller IC 33, a controller IC for a general-purpose electrostatic-capacity-type touch sensor may be used.

The CPU 34 processes data supplied from the sensor 10, the GPS unit 211, the wireless communication unit 212, the NFC communication unit 216, the motion sensor 220, and the like.

[Effects]

For the wristwatch-type electronic device 200 according to the fifth embodiment, the band 202 includes the sensor 10 according to the first embodiment.

Therefore, part or all of operations generally performed on a touch panel or the like on a screen can be replaced with the operation area R10 of the band 202. As a result, an operation can be performed without hiding the screen with a finger, whereby usability can be improved.

Furthermore, use of the sensor 10 according to the first embodiment instead of a mere electrostatic-capacity-type touch sensor enables an input operation with a higher degree of flexibility, such as a fine operation with the tip of a nail or a multistage input by pressing.

Modified Examples

In the fifth embodiment, the example in which the present technology is applied to the wristwatch-type electronic device 200 has been described. However, the present technology is not limited to this example and applicable to various electronic devices (wearable terminals) attachable to and detachable from the human body. For example, the present technology is also applicable to a band-type electronic device such as a smart band, a bracelet-type electronic device, a ring-type electronic device, an eyeglass-type electronic device, a shoe-type electronic device, a garment-type electronic device, and the like. Moreover, the present technology is also applicable to a head mounted display and the like.

Sensing a pressure distribution inside the band 202 may be performed with the sensor 10 included in the band 202. This enables reading of the shape of the muscle and the tendon, and estimation of what the wearer of the wristwatch-type electronic device 200 is currently doing from the posture of the arm and the posture of the finger. Furthermore, consciously moving the arm and the hand enables control of the device with only one arm wearing the device. Such a detecting operation is difficult to perform with a general touch sensor, and is a strength unique to a pressure distribution sensor. There is a method of detecting myoelectricity as a method of sensing a movement of the arm. However, the myoelectricity has a large noise due to the degree of skin contact, sweating situations, or the like. Note that the above-described pressure distribution sensing may be performed with a band-type electronic device such as a smart band, a bracelet-type electronic device, or the like.

Instead of the sensor 10 according to the first embodiment, the wristwatch-type electronic device 200 may include the sensor 10 according to the modified examples of the first embodiment, the sensor 10A according to the second embodiment, the sensor 10A according to the modified examples of the second embodiment, the sensor 10B according to the third embodiment, the sensor 10B according to the modified examples of the third embodiment, or the sensor 110 according to the fourth embodiment.

The sensor 10 may be a so-called biosensor. In this case, the controller IC 33 may detect the heartbeat, pulse, or the like of the user wearing the wristwatch-type electronic device 200, on the basis of an output signal supplied from the sensor 10, and may issue a notification for the detection result to the CPU 34.

At least one of the band 202 or the band 203 may further include a bending sensor, and the main body unit 201 may further include a controller IC for the bending sensor. In this case, the controller IC may detect a wearing state of the wristwatch-type electronic device 200, on the basis of an output signal from the bending sensor.

EXAMPLE

The present technology will be specifically described below with reference to an example; however, the present technology is not limited to only the example.

Example

The members indicated in Table 1 were used to prepare a pressure distribution sensor having the configuration illustrated in FIG. 1.

Table 1 indicates the configuration of the flexible pressure distribution sensor.

TABLE 1

| Layer | Material | Thickness [μm] |
| --- | --- | --- |
| Reference electrode layer | Metal-deposited fabric | 100 |
| Adhesive layer | Pressure-sensitive adhesive film | 30 |
| Deformable layer | Polyurethane foam material | 200 |
| Adhesive layer | Pressure-sensitive adhesive film | 30 |
| Sensor electrode layer | FPC | 85 |
| Adhesive layer | Pressure-sensitive adhesive film | 30 |
| Deformable layer | Polyurethane foam material | 200 |
| Adhesive layer | Pressure-sensitive adhesive film | 30 |
| Reference electrode layer | Metal-deposited fabric | 100 |

(Evaluation) The prepared pressure distribution sensor was repeatedly wound around a columnar body having a diameter similar to a wrist, and then visual confirmation was performed whether or not separation occurred between the layers included in the sensor. As a result, no separation was confirmed between the layers.

The embodiments of the present technology and the modified examples thereof have been concretely described above. However, the present technology is not limited to the above-described embodiments and the modified examples thereof, and various modifications based on the technical idea of the present technology can be made.

For example, the configurations, methods, processes, shapes, materials, numerical values, and the like described in the above embodiments and the modified examples thereof are merely examples, and configurations, methods, processes, shapes, materials, numerical values, and the like different from those described in the above-described embodiments and the modified examples thereof may also be used as necessary.

Furthermore, the configurations, methods, processes, shapes, materials, numerical values, and the like of the above-described embodiments and modifications thereof can be combined with each other, without departing from the gist of the present technology.

Furthermore, the present technology can also adopt the following configurations.

(1)
A sensor including:
an electrostatic-capacity-type sensor electrode layer having a plurality of sensing units;
a reference electrode layer opposed to one main face of the sensor electrode layer; and
a deformable layer disposed between the reference electrode layer and the sensor electrode layer, the deformable layer being to deform elastically due to application of pressure,
in which the deformable layer is recessed between the sensing units or discontinuous between the sensing units, and
the reference electrode layer has a shaped portion between the sensing units.

(2)
The sensor according to (1), in which the shaped portion is bent in a recessed shape, a protruding shape, or an uneven shape.

(3)
The sensor according to (1), in which the shaped portion is curved in an arch shape toward the sensor electrode layer.

(4)
The sensor according to (1), in which the shaped portion is bent in a recessed shape, and
the shaped portion is stuck to a portion between the sensing units.

(5)
The sensor according to (1), in which the shaped portion is extensible and contractible.

(6)
The sensor according to (5), in which the shaped portion has a corrugated shape.

(7)
The sensor according to (1), in which the reference electrode layer is an uneven layer having a protruding shape at a position opposed to each of the sensing units and having a recessed shape at an opposed position between the sensing units, and
the recessed portion is the shaped portion.

(8)
The sensor according to claim 1, in which each of the sensing units is a first sensing unit,
the sensor electrode layer further has a plurality of second sensing units, and
the second sensing units each are disposed between the first sensing units.

(9)
The sensor according to any of (1) to (8), in which the reference electrode layer is opposed to part of the one main face of the sensor electrode layer.

(10)
The sensor according to any of (1) to (9), in which the plurality of sensing units is disposed one-dimensionally or two-dimensionally.

(11)
The sensor according to any of (1) to (10), in which the deformable layer includes a dielectric.

(12)
The sensor according to (11), in which the dielectric is a foamed resin or an insulating elastomer.

(13)
A sensor including:
an electrostatic-capacity-type sensor electrode layer having a plurality of sensing units;
a first reference electrode layer opposed to a first main face of the sensor electrode layer;
a second reference electrode layer opposed to a second main face of the sensor electrode layer;
a first deformable layer disposed between the first reference electrode layer and the sensor electrode layer, the first deformable layer being to deform elastically due to application of pressure; and
a second deformable layer disposed between the second reference electrode layer and the sensor electrode layer, the second deformable layer being to deform elastically due to application of pressure,
in which the first deformable layer and the second deformable layer are recessed between the sensing units or discontinuous between the sensing units, and
the first reference electrode layer and the second reference electrode layer each have a shaped portion between the sensing units.

(14)
A sensor including:
an electrostatic-capacity-type sensor electrode layer having a plurality of sensing units;
a reference electrode layer opposed to one main face of the sensor electrode layer; and
a plurality of elastic members,
in which the elastic members each are provided between the reference electrode layer and the sensing unit, and
the reference electrode layer has a shaped portion between the sensing units.

(15)
The sensor according to (14), in which each of the elastic members is a columnar body or a spring-shaped member.

(16)
A band including the sensor according to any of (1) to (15).

(17)
An electronic device including the sensor according to any of (1) to (15).

(18)
The electronic device according to (17), in which the electronic device is attachable to and detachable from a human body.

(19)
A wristwatch-type electronic device including a band having the sensor according to any of (1) to (15).

REFERENCE SIGNS LIST 10, 10A, 10B, 110 Sensor
11, 13, 41, 42 Electrode base
11a, 13a Opposed portion
11b, 13b Shaped portion
11c, 13c, 21 Base
11d, 13d Reference electrode layer
12, 14 Deformable layer
20, 40, 50 Sensor electrode layer
20s, 40s, 50s Sensing unit
22, 52, 41b Pulse electrode
23, 53, 42b Sense electrode
24 Insulating layer
201 Wristwatch-type electronic device
201 Main body unit
202, 203 Band

What is claimed is:
1. A sensor comprising:
an electrostatic-capacity-type sensor electrode layer having a plurality of sensing units, wherein the plurality of sensing units each include a first electrode and a second electrode, and wherein the first electrode and the second electrode have a comb-teeth shape;
a reference electrode layer opposed to one main face of the electrostatic-capacity-type sensor electrode layer; and
a deformable layer disposed between the reference electrode layer and the electrostatic-capacity-type sensor electrode layer, the deformable layer deformable elastically due to application of pressure,
wherein the deformable layer is recessed between each of the plurality of sensing units or discontinuous between each of the plurality of sensing units,
wherein the reference electrode layer is continuous between the each of the plurality of sensing units, and
wherein the reference electrode layer has a shaped portion between each of the plurality of sensing units.

2. The sensor according to claim 1, wherein the shaped portion is bent in a recessed shape, a protruding shape, or an uneven shape.

3. The sensor according to claim 1, wherein the shaped portion is curved in an arch shape toward the sensor electrode layer.

4. The sensor according to claim 1, wherein the shaped portion is bent in a recessed shape, and
the shaped portion is stuck to a portion between each of the plurality of sensing units.

5. The sensor according to claim 1, wherein the shaped portion is extensible and contractible.

6. The sensor according to claim 5, wherein the shaped portion has a corrugated shape.

7. The sensor according to claim 1, wherein the reference electrode layer is an uneven layer having a protruding shape at a position opposed to each of the plurality of sensing units and having a recessed shape at an opposed position between each of the plurality of sensing units, and
the recessed portion is the shaped portion.

8. The sensor according to claim 1, wherein the plurality of sensing units are a plurality of first sensing units,
the electrostatic-capacity-type sensor electrode layer further including a plurality of second sensing units, and
the plurality of second sensing units each are disposed between the each of the plurality of first sensing units.

9. The sensor according to claim 1, wherein the reference electrode layer is opposed to part of the one main face of the electrostatic-capacity-type sensor electrode layer.

10. The sensor according to claim 1, wherein the plurality of sensing units are disposed one-dimensionally or two-dimensionally.

11. The sensor according to claim 1, wherein the deformable layer includes a dielectric.

12. The sensor according to claim 11, wherein the dielectric is a foamed resin or an insulating elastomer.

13. A band comprising the sensor according to claim 1.

14. An electronic device comprising the sensor according to claim 1.

15. The electronic device according to claim 14, wherein the electronic device is attachable to and detachable from a human body.

16. A wristwatch-type electronic device comprising a band having the sensor according to claim 1.

17. A sensor comprising:
an electrostatic-capacity-type sensor electrode layer having a plurality of sensing units, wherein the plurality of sensing units each include a first electrode and a second electrode, and wherein the first electrode and the second electrode have a comb-teeth shape;
a first reference electrode layer opposed to a first main face of the electrostatic-capacity-type sensor electrode layer;
a second reference electrode layer opposed to a second main face of the electrostatic-capacity-type sensor electrode layer;
a first deformable layer disposed between the first reference electrode layer and the electrostatic-capacity-type sensor electrode layer, the first deformable layer deformable elastically due to application of pressure; and
a second deformable layer disposed between the second reference electrode layer and the electrostatic-capacity-type sensor electrode layer, the second deformable layer deformable elastically due to application of pressure,
wherein the first deformable layer and the second deformable layer are recessed between each of the plurality of sensing units or discontinuous between each of the plurality of sensing units,
wherein the first reference electrode layer is continuous between the each of the plurality of sensing units, and
wherein the first reference electrode layer and the second reference electrode layer each have a shaped portion between each of the plurality of sensing units.

18. A sensor comprising:
an electrostatic-capacity-type sensor electrode layer having a plurality of sensing units, wherein the plurality of sensing units each include a first electrode and a second electrode, and wherein the first electrode and the second electrode have a comb-teeth shape;
a reference electrode layer opposed to one main face of the electrostatic-capacity-type sensor electrode layer; and
a plurality of elastic members,
wherein the plurality of elastic members each are provided between the reference electrode layer and the plurality of sensing units,
wherein the reference electrode layer is continuous between the each of the plurality of sensing units, and
wherein the reference electrode layer has a shaped portion between each of the plurality of sensing units.

19. The sensor according to claim 18, wherein each of the plurality of elastic members is a columnar body or a spring-shaped member.

* * * * *